US007790693B2

(12) United States Patent
Czech et al.

(10) Patent No.: US 7,790,693 B2
(45) Date of Patent: Sep. 7, 2010

(54) GLUCOSE-TRANSPORT RELATED GENES, POLYPEPTIDES, AND METHODS OF USE THEREOF

(75) Inventors: Michael P. Czech, Westborough, MA (US); Aimee Powelka, Framingham, MA (US); Adilson L. Guilherme, Shrewsbury, MA (US); Xiaoqing Tang, Lexington, KY (US)

(73) Assignee: University of Massachusetts, Boston, MA (US)

( * ) Notice: Subject to any disclaimer, the term of this patent is extended or adjusted under 35 U.S.C. 154(b) by 444 days.

(21) Appl. No.: 11/292,549

(22) Filed: Dec. 2, 2005

(65) Prior Publication Data

US 2006/0160133 A1    Jul. 20, 2006

Related U.S. Application Data

(60) Provisional application No. 60/632,462, filed on Dec. 2, 2004.

(51) Int. Cl.
*A61K 31/70*    (2006.01)
*C07H 21/02*    (2006.01)
*C12Q 1/54*    (2006.01)
*C12N 5/00*    (2006.01)

(52) U.S. Cl. ................ 514/44 A; 435/14; 435/375; 514/44 R; 536/23.1

(58) Field of Classification Search .................. None
See application file for complete search history.

(56) References Cited

U.S. PATENT DOCUMENTS

| 6,346,374 | B1 | 2/2002 | Tartaglia et al. |
|---|---|---|---|
| 2003/0153519 | A1 | 8/2003 | Kay et al. |
| 2004/0198682 | A1 | 10/2004 | McSwiggen et al. |

FOREIGN PATENT DOCUMENTS

| WO | 02/33046 | 4/2002 |
|---|---|---|
| WO | WO 02/103361 A1 * | 12/2002 |
| WO | 2004/053103 | 6/2004 |

OTHER PUBLICATIONS

Tesz et al., Tumor Necrosis Factor alpha (TNFalpha) stimulates MAP4K4 expression through TNF alpha receptor 1 signaling to c-Jun and activating transcription factor 2, 2007, The Journal of Biological Chemistry, vol. 282, No. 27, pp. 19302-19312.*
Tang et al, An RNA interference-based screen identifies MAP4K4/NIK as a negative regulator of PPARg adipogenesis, and insulin-responsive hexose transport, 2006, PNAS, vol. 103, Issue 7, pp. 2087-2092.*
Bork et al., Go hunting in sequence databases but watch out for the traps, 1996, Trends in Genetics, vol. 12, pp. 425-427.*
Bork, Powers and Pitfalls in Sequence Analysis: the 70% hurdle, 2000, Genome Research, vol. 10, pp. 398-400.*
Brenner, Errors in genome annotation, 1999, Trends in Genetics, vol. 15, pp. 132-133.*
Doerks et al., Protein annotation: detective work for function prediction, 1998, Trends in Genetics, vol. 14, pp. 248-250.*
Ngo et al., The protein folding problem and tertiary structure prediction,1994, pp. 492-495.*
Skolnick et al., From genes to protein structure and function: novel applications of computational approaches in the genomic era, 2000, Trends in Biotech, vol. 18, Issue 1, pp. 34-39.*
Smith et al., The challenge of genome sequence annotation or "The devil is in the details", 1997, Nature Biotechnology, vol. 15, pp. 1222-1223.*
Wells et al., Addivity of mutational effects in proteins, 1990, Biochemistry, vol. 29, pp. 8509-8517.*
Aagaard et al., RNAi therapeutics: principles, prospects and challenges, 2007, Advanced Drug Delivery Reviews, vol. 59, pp. 75-86.*
Leung et al., RNA interference: from gene silencing to gene-specific therapeutics, 2005, Pharmacology and Therapeutics, vol. 107, pp. 222-239.*
Su et al. 1997, EMBO Journal, vol. 16, No. 6, pp. 1279-1290.*
Bjorkman et al. "Genomic Structure of PEX13, a Candidate Peroxisome Biogenesis Disorder Gene" Genomics, 54:521-528, 1998.
Liu et al., "PEX 13 is Mutated in Complementation Group 13 of the Peroxisome-Biogenesis Disorders" Am. J. Hum. Genet. 65:621-634, 1999.
European Search Report, Application No. 05852901.7, May 4, 2009.
Moyersoen et al., "Biogenesis of peroxisomes and glycosomes: trypanosomatid glycosome assembly is a promising new drug target," FEMS Microbiology Reviews, 28(5):603-643 (2004).
Besset et al., "The Identification and Characterization of Expression of *Pftaire-1*, a Novel Cdk Family Member, Suggest Its Function in the Mouse Testis and Nervous System," *Molecular Reproduction and Development*, vol. 50:18-29 (1998).
Caldas et al., "NSDHL, an enzyme involved in cholesterol biosynthesis, traffics through the Golgi and accumulates on ER membranes and on the surface of lipid droplets," *Human Molecular Genetics*, vol. 12:2981-2991 (2003).
Czech et al., "Signaling Mechanisms That Regulate Glucose Transport," *The Journal of Biological Chemistry*, vol. 274:1865-1868 (1999).
Danesch et al., "Cloning and Transcriptional Regulation of a Novel Adipocyte-specific Gene, *FSP27*," *The Journal of Biological Chemistry*, vol. 267:7185-7193 (1992).
Elmendorf et al., "Insulin Signaling Regulating the Trafficking and Plasma Membrane Fusion of GLUT4-Containing Intracellular Vesicles," *Experimental Cell Research*, vol. 253:55-62 (1999).
Enari et al., "A caspase-activated DNase that degrades DNA during apoptosis, and its inhibitor ICAD," *Nature*, vol. 391:43-50 (1998).
Gentlemen et al., "Bioconductor: open software development for computational biology and bioinformatics," *Genome Biology*, vol. 5:R80 (2004).
Graeser et al., "Regulation of the CDK-related protein kinase PCTAIRE-1 and its possible role in neurite outgrowth in Neuro-2A cells," *Journal of Cell Science*, vol. 115:3479-3490 (2002).

(Continued)

*Primary Examiner*—Robert Landsman
*Assistant Examiner*—Ian Dang
(74) *Attorney, Agent, or Firm*—Fish & Richardson P.C.

(57) ABSTRACT

Methods and compositions for modulating glucose transport are provided herein.

3 Claims, 9 Drawing Sheets

OTHER PUBLICATIONS

Guilherme et al., "EHD2 and the Novel EH Domain Binding Protein EHBP1 Couple Endocytosis to the Actin Cytoskeleton," *The Journal of Biological Chemistry*, vol. 279:10593-10605 (2004).

Hotamisligil et al., "Increased Adipose Tissue Expression of Tumor Necrosis Factor-α in Human Obesity and Insulin Resistance," *J. Clin. Invest.*, vol. 95:2409-2415 (1995).

Jiang et al., "Insulin signaling through Akt/protein kinase B analyzed by small interfering RNA-mediated gene silencing," *PNAS*, vol. 100:7569-7574 (2003).

Joberty et al., "The cell-polarity protein Par6 links Par3 and atypical protein kinase C to Cdc42," *Nature Cell Biology*, vol. 2:531-539 (2000).

Kirikoshi et al., "Molecular Cloning and Characterization of Human Frizzled-4 on Chromosome 11q14-q21," *Biochemical and Biophysical Research Communication*, vol. 264:955-961 (1999).

Kishida et al., "Wnt-3a and Dvl Induce Neurite Retraction by Activating Rho-Associated Kinase," *Molecular and Cellular Biology*, vol. 24:4487-4501 (2004).

Kolle et al., "*CRIM1*, a novel gene encoding a cysteine-rich repeat protein, is developmentally regulated and implicated in vertebrate CNS development and organogenesis," *Mechanisms of Development*, vol. 90:181-193 (2000).

Krylova et al., "Dishevelled-1 Regulates Microtubule Stability: A New Function Mediated by Glycogen Synthase Kinase-3β," *The Journal of Cell Biology*, vol. 151:83-93 (2000).

Le et al., "Insulin signaling and glucose homeostasis in mice lacking protein tyrosine phosphatase α," *Biochemical and Biophysical Research Communications*, vol. 314:321-329 (2004).

Lee et al., "c-Jun N-terminal Kinase (JNK) Mediates Feedback Inhibition of the Insulin Signaling Cascade," *The Journal of Biological Chemistry*, vol. 278:2896-2902 (2003).

Liang et al., "Molecular cloning and characterization of CIDE-3, a novel member of the cell-death-inducing DNA-fragmentation-factor (DFF45)-like effector family," *Biochem J.*, vol. 370:195-203 (2003).

Martin et al., "GLUT4 Trafficking in Insulin-Sensitive Cells," *Cell Biochemistry and Biophysics*, vol. 30:89-113 (1999).

McCaffrey et al., "RNA interference in adult mice," *Nature*, vol. 418:38-39 (2002).

Mercurio et al., "IKK-1 and IKK-2: Cytokine-Activated IκB Kinases Essential for NF-κB Activation," *Science*, vol. 278:860-866 (1997).

Meyerson et al., "A family of human cdc2-related protein kinases," *The EMBO Journal*, vol. 11:2909-2917 (1992).

Miyamoto et al., "Azoospermia in patients heterozygous for a mutation in SYCP3," *The Lancet*, vol. 362:1714-1719, 2003.

Morrison et al., "Hormonal Signaling and Transcriptional Control of Adipocyte Differentiation," *The Journal of Nutrition*, vol. 130:3116S-3121S (2000).

Okuda et al., "*PCTAIRE-1* and *PCTAIRE-3*, two members of a novel *cdc2/CDC28*-related protein kinase gene family," *Oncogene*, vol. 7:2249-2258 (1992).

Phan et al., "Lipin Expression Preceding Peroxisome Proliferator-activated Receptor-γ Is Critical for Adipogenesis in Vivo and in Vitro," *The Journal of Biological Chemistry*, vol. 279:29558-29564 (2004).

Richard et al., "ABC50, a Novel Human ATP-Binding Cassette Protein Found in Tumor Necrosis Factor-α-Stimulated Synoviocytes," *Genomics*, vol. 53:137-145 (1998).

Robitaille et al., "Mutant frizzled-4 disrupts retinal angiogenesis in familial exudative vitreoretinopathy," *Nature Genetics*, vol. 32:326-330 (2002).

Ross et al., "Inhibition of Adipogenesis by Wnt Signaling," *Science*, vol. 289:950-953 (2000).

Sakahira et al., "Cleavage of CAD inhibitor in CAD activation and DNA degradation during apoptosis," *Nature*, vol. 391:96-99 (1998).

Sakai et al., Integrin-linked kinase (ILK) is required for polarizing the epiblast, cell adhesion, and controlling actin accumulation, *Genes & Development*, vol. 17:926-940 (2003).

Stephens et al., "Tumor Necrosis Factor-α-induced Insulin Resistance in 3T3-L1 Adipocytes Is Accompanied by a Loss of Insulin Receptor Substrate-1 and GLUT4 Expression without a Loss of Insulin Receptor-mediated Signal Transduction," *The Journal of Biological Chemistry*, vol. 272:971-976 (1997).

Su et al., "NIK is a new Ste20-related kinase that binds NCK and MEKK1 and activates the SAPK/JNK cascade via a conserved regulatory domain," *The EMBO Journal*, vol. 16:1279-1290 (1997).

Tamori et al., "Role of Peroxisome Proliferator-Activated Receptor-γ in Maintenance of the Characteristics of Mature 3T3-L1 Adipocytes," *Diabetes*, vol. 51:2045-2055 (2002).

Wang et al., "A PCR primer bank for quantitative gene expression analysis," *Nucleic Acids Research*, vol. 31:e154 (2003).

Wellen et al., "Obesity-induced inflammatory changes in adipose tissue," *The Journal of Clinical Investigation*, vol. 112:1785-1788 (2003).

Xue et al., "Mesodermal patterning defect in mice lacking the Ste20 NCK interacting kinase (NIK)," *Development*, vol. 128:1559-1572 (2001).

Yao et al., "A Novel Human STE20-related Protein Kinase, HGK, That Specifically Activates the c-Jun N-terminal Kinase Signaling Pathway," *The Journal of Biological Chemistry*, vol. 274:2118-2125 (1999).

Zhang et al., "Negative Regulation of Peroxisome Proliferator-Activated Receptor-γ Gene Expression Contributes to the Antiadipogenic Effects of Tumor Necrosis Factor-α," *Molecular Endocrinology*, vol. 10:1457-1466 (2007).

GenBank Accession No. BC023683, 3 pages (Feb. 5, 2002).
GenBank Accession No. NM_178050, 4 pages (1999).
GenBank Accession No. BC057074, 4 pages (2002).
GenBank Accession No. NM_178373, 3 pages (1992).
GenBank Accession No. AY364640, 2 pages (2003).
GenBank Accession No. NM_008055, 4 pages (1996).
GenBank Accession No. AB032417, 4 pages (Sep. 14, 1999).
GenBank Accession No. NM_011517, 4 pages (1997).
GenBank Accession No. NM_153694, 4 pages (2000).
GenBank Accession No. M36033, 3 pages (Apr. 11, 1990).
GenBank Accession No. NM_007700, 6 pages (1995).
GenBank Accession No. NM-001278, 6 pages (1993).
GenBank Accession No. NM_008696, 8 pages (1997).
GenBank Accession No. NM_145686, 9 pages (1997).
GenBank Accession No. NM_011049, 5 pages (1992).
GenBank Accession No. X66363, 2 pages (1992).
GenBank Accession No. NM_008795, 4 pages (1992).
GenBank Accession No. NM_212502, 6 pages (1992).
GenBank Accession No. NM_011074, 5 pages (1997).
GenBank Accession No. NM_016700, 5 pages (1997).
GenBank Accession No. NM_016961, 5 pages (1996).
GenBank Accession No. NM_022801, 5 pages (1988).
GenBank Accession No. NM_008363, 6 pages (1996).
GenBank Accession No. NM_019730, 3 pages (2000).
GenBank Accession No. AK078461, 5 pages (Apr. 16, 2002).
GenBank Accession No. NM_028385, 6 pages (2001).
GenBank Accession No. AK129472, 3 pages (Jul. 23, 2003).
GenBank Accession No. NM_025670, 3 pages (2002).
GenBank Accession No. BC063094, 4 pages (Dec. 2, 2003).
GenBank Accession No. BC024811, 3 pages (Mar. 1, 2002).
GenBank Accession No. AK018652, 5 pages, (Jul. 10, 2000).
GenBank Accession No. BC059190, 4 pages (Oct. 1, 2003).
GenBank Accession No. BC015285, 3 pages (Oct. 1, 2001).
GenBank Accession No. XM_128751, 4 pages (2005).
GenBank Accession No. U10115, 3 pages (1992).
GenBank Accession No. AF180471, 4 pages (Aug. 24, 1999).
GenBank Accession No. NM_010941, 4 pages (1975).
GenBank Accession No. NM_010562, 5 pages (1997).
GenBank Accession No. NM_053117, 3 pages (2000).

* cited by examiner

GLUCOSE-TRANSPORT RELATED GENES, POLYPEPTIDES, AND METHODS OF USE THEREOF

CROSS-REFERENCE TO RELATED APPLICATIONS

This application claims the benefit of priority of U.S. Provisional Patent Application No. 60/632,462, filed Dec. 2, 2004, the contents of which are hereby incorporated by reference in their entirety.

The work described herein was funded, in part, through grants from the National Institutes of Health (Grant Nos. DK30898 and DK60837-03). The United States government may, therefore, have certain rights in the invention.

TECHNICAL FIELD

This invention relates to molecular biology, cell biology, glucose transport, and diabetes.

BACKGROUND

Insulin stimulates glucose transport in muscle and fat. One of the most critical pathways that insulin activates is the rapid uptake of glucose from the circulation in both muscle and adipose tissue. Most of insulin's effect on glucose uptake in these tissues is dependent on the insulin-sensitive glucose transporter, GLUT4 (reviewed in Czech and Corvera, 1999, *J. Biol. Chem.*, 274:1865-1868, Martin et al., 1999, *Cell Biochem. Biophys.*, 30:89-113, Elmendorf et al., 1999 *Exp. Cell Res.*, 253:55-62). The mechanism of insulin action is impaired in diabetes, leading to less glucose transport into muscle and fat. This is thought to be a primary defect in type II diabetes. Potentiating insulin action has a beneficial effect on type II diabetes. This is believed to be the mechanism of action of the drug Rezulin (troglitazone).

Type II diabetes mellitus (non-insulin-dependent diabetes) is a group of disorders, characterized by hyperglycemia that can involve an impaired insulin secretory response to glucose and insulin resistance. One effect observed in type II diabetes is a decreased effectiveness of insulin in stimulating glucose uptake by skeletal muscle. Type II diabetes accounts for about 85-90% of all diabetes cases. In some cases of type II diabetes the underlying physiological defect appears to be multifactoral.

SUMMARY

The invention is based, at least in part, on the discovery of gene products that regulate glucose transport in cells. The genes and gene products described herein are novel targets for modulation for the treatment of disorders in which glucose metabolism is disregulated, such as diabetes.

Accordingly, in one aspect, the invention features methods for identifying a candidate agent that modulates expression or activity of a glucose transport-related polypeptide. The methods include, for example: (a) providing a sample including a glucose-transport related polypeptide or a nucleic acid encoding the polypeptide, wherein the glucose-transport related polypeptide is a gene product of a gene in Table 1 or Table 2, or a homolog thereof (e.g., a human homolog); (b) contacting the sample with a test compound; (c) evaluating expression or activity of the glucose transport-related polypeptide in the sample; and (d) comparing the expression or activity of the glucose transport-related polypeptide of (c) to expression or activity of the glucose transport-related polypeptide in a control sample lacking the test compound, wherein a change in glucose transport-related polypeptide expression or activity indicates that the test compound is a candidate agent that can modulate the expression or activity of the glucose transport-related polypeptide.

In various embodiments, the glucose transport-related polypeptide is a gene product of a gene in Table 1, e.g., Peroxin 13 (Pex13), ADP-ribosylation factor-like 6 interacting protein (Arl6ip2), Superoxide dismutase 1 (SOD), a product of Fat specific gene 27 (FSP27), Frizzled homolog 4 (Fzd4), Synaphin 3 (Sycp3), Protein tyrosine phosphatase receptor type A (Ptpra), Conserved helix-loop-helix ubiquitous kinase (Chuk, or IKKα), Mitogen-activated protein kinase kinase kinase kinase 4 (Map4k4), PCTAIRE-motif protein kinase 1 (Pctk1), PCTAIRE-motif protein kinase 3 (Pctk3), PFTAIRE protein kinase 1 (Pftk1), Mitogen activated protein kinase 8 (JNK1), Mitogen activated protein kinase 9 (JNK2), MAP/microtubule affinity-regulating kinase 3 (Mark3), Interleukin-1 receptor-associated kinase 1 (IRAK1), or Expressed in non-metastatic cells 3 (Nme3). In various embodiments, the glucose transport-related polypeptide includes an amino acid sequence at least 50, 60, 70, 80, 90, 95, 96, 99, or 100% identical to the gene product of a gene in Table 1. The polypeptide can be a human polypeptide (e.g., a human polypeptide encoded by a gene in Table 1 or a human homolog of a gene in Table 1).

In various embodiments, the glucose transport-related polypeptide is a gene product of a gene in Table 2, e.g., a gene product of one of the following clones from The Institute of Physical and Chemical Research (RIKEN): 9130022E05Rik, 2900045N06Rik, 4930402E16Rik, 5730403B10Rik, F830029L24Rik, G430055L02Rik, or a human homolog thereof; or the gene product is ATP-binding cassette, sub family F (Abcf1), Cysteine-rich motor neuron 1 (Crim1), Dishevelled segment polarity protein homolog (Dvl1), NAD (P) dependent steroid dehydrogenase-like protein (Nsdhl), Integrin linked kinase (Ilk), Par-6 partitioning defective 6 homolog gamma (Pard6g), or Lipin (Lpin1); or the gene product of D11Ertd498 or D19Ertd703e. In various embodiments, the glucose transport-related polypeptide includes an amino acid sequence at least 50, 60, 70, 80, 90, 95, 96, 99, or 100% identical to the gene product of a gene in Table 2.

The sample used in the methods can be or include a cell (e.g., an adipocyte) or can be a cell-free sample. The expression or activity of the glucose transport-related polypeptide can be evaluated, e.g., using a cell-free or cell-based assay. Modulation of expression can be evaluated using an antibody. In one embodiment, the evaluating includes determining whether glucose transport is modulated in the presence of the test compound, e.g., by determining glucose uptake.

The test compound evaluated in the method can be a polynucleotide, a polypeptide, a small non-nucleic acid organic molecule, a small inorganic molecule, or an antibody. For example, the test compound can be an antisense oligonucleotide, an inhibitory RNA, or a ribozyme.

Glucose transport may be increased or decreased in the presence of the test compound.

In various embodiments, the glucose transport-related polypeptide is a kinase. In such embodiments, the evaluating can include determining phosphorylation of a substrate by the kinase, e.g., using a kinase assay.

The methods can include steps in which the effect of the test compound on expression or activity of the glucose transport-related polypeptide is evaluated in vivo, e.g., using an animal model, such as an animal model of diabetes.

In another aspect, the invention features methods for modulating glucose transport in a cell. These methods include, for example; providing a cell; contacting the cell (e.g., in vitro or in vivo) with an agent that modulates expression or activity of a glucose transport-related polypeptide, thereby modulating glucose transport in the cell.

The test compound that modulates expression or activity of a glucose transport-related polypeptide can be an agent identified by a method described herein, e.g., a method including the following steps: (a) providing a sample including the glucose-transport related polypeptide or a nucleic acid encoding the polypeptide; (b) contacting the sample with a test compound; (c) evaluating expression or activity of the glucose transport-related polypeptide in the sample; and (d) comparing the expression or activity of the glucose transport-related polypeptide of (c) to expression or activity of the glucose transport-related polypeptide in a control sample lacking the test compound, wherein a change in glucose transport-related polypeptide expression or activity indicates that the test compound is a candidate agent that can modulate the expression or activity of the glucose transport-related polypeptide.

The test compound employed in the method of modulating glucose transport in a cell can modulate the expression or activity of a gene product of a gene in Table 1 or Table 2. The test compound may decrease or increase expression or activity of a gene product of a gene in Table 1. The test compound can be a polynucleotide, a polypeptide, a small non-nucleic acid organic molecule, a small inorganic molecule, and an antibody. For example, the test compound is a small inhibitory RNA. The test compound can be selected from the group consisting of an antisense oligonucleotide, an inhibitory RNA, or a ribozyme.

The methods for modulating glucose transport in a cell can further include contacting the cell with a second agent that modulates expression or activity of a glucose transport-related polypeptide.

The invention also features methods for increasing insulin-stimulated glucose uptake in a subject. The methods include: administering to the subject an agent that decreases expression or activity of a gene product of a gene in Table 1 in an amount sufficient to modulate glucose metabolism in a cell of the subject, thereby increasing insulin-stimulated glucose uptake in the subject. For example, the subject can be at risk for or suffering from a disorder or condition related to glucose metabolism such as type I diabetes, type II diabetes, or obesity.

The invention also provides methods for modulating glucose metabolism in a subject by administering to the subject an agent that increases expression or activity of a gene product of a gene in Table 2 in an amount sufficient to modulate glucose metabolism in a cell of the subject, thereby modulating glucose metabolism in the subject.

Also featured herein are compositions that include a nucleic acid encoding an inhibitory RNA that targets an RNA encoded by a gene of Table 1. In one embodiment, the inhibitory RNA is a small inhibitory RNA.

The invention further provides compositions that include an antisense nucleic acid that inhibits the function of a gene product of a gene of Table 1.

The invention also features methods for diagnosing a disorder or condition related to glucose metabolism by evaluating the expression or activity of one or more gene products of the genes in Tables 1 and 2.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting. All cited patents, patent applications, and references (including references to public sequence database entries) are incorporated by reference in their entireties for all purposes. U.S. Provisional App. No. 60/632,462, filed Dec. 2, 2004, is incorporated by reference in its entirety for all purposes.

BRIEF DESCRIPTION OF THE DRAWINGS

Like reference symbols in the various drawings indicate like elements.

DETAILED DESCRIPTION

Figure 1:
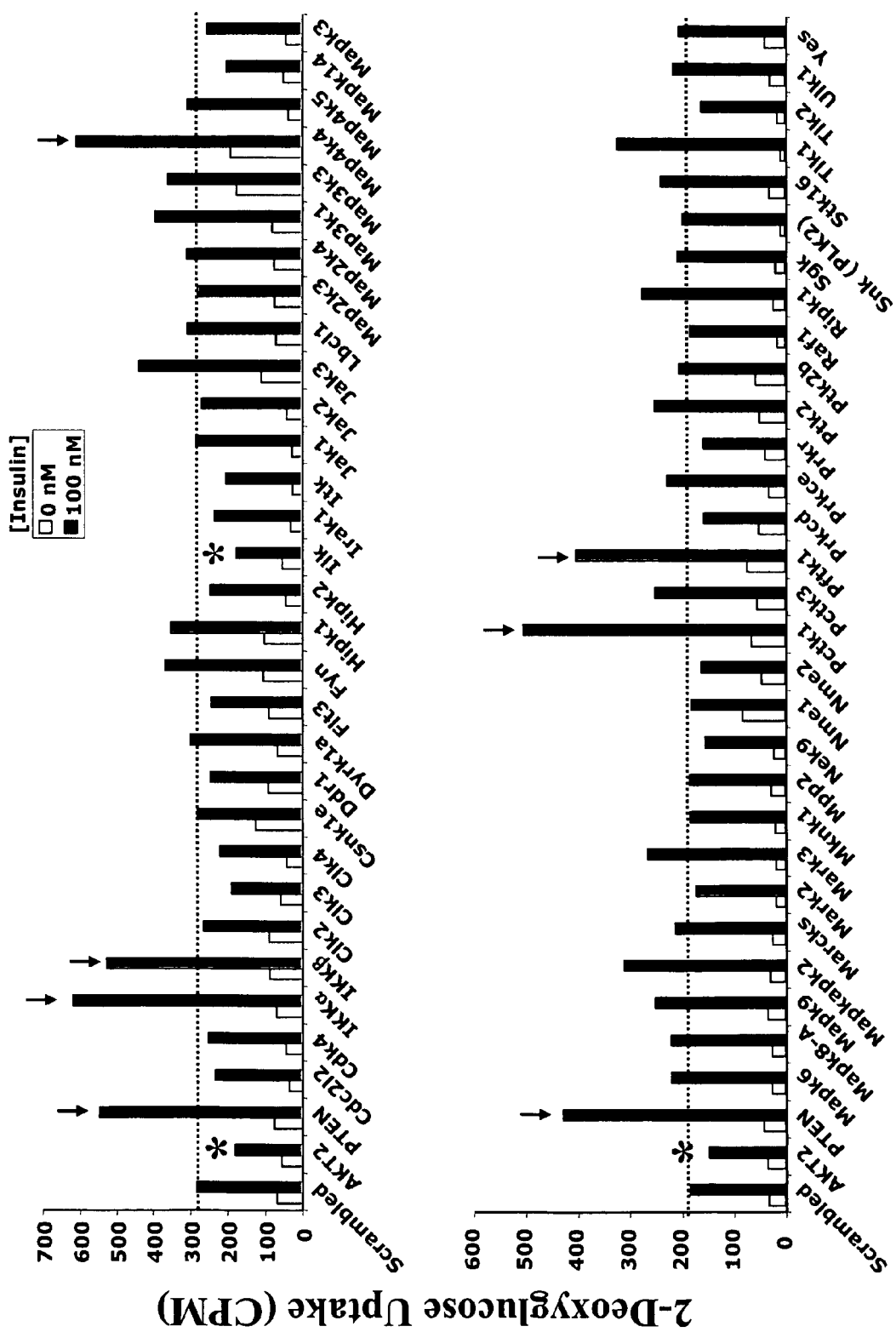
FIG. 1 is a set of graphs depicting the levels and dose dependence of insulin-stimulated deoxyglucose uptake in cells transfected with siRNAs. Cells were transfected with scrambled (6 nmol), Akt1+Akt2, (4+6 nmol), or PTEN (6 nmol) as controls, and indicated SMARTpool® (6 nmol) siRNAs, stimulated with insulin, and assayed by determining counts per minute (CPMs) of radioactive deoxyglucose uptake in cells treated with controls siRNA or indicated SMARTpool® siRNAs. The names of each gene product identified by the screen are listed on the X axes. Protein kinase hits, indicated by the letters arrows and asterisks, were identified using this strategy. The data represents the average of 3 independent screening experiments.

We have identified genes, the polypeptide products of which regulate glucose transport in adipocytes in response to insulin signals. Here, we provide methods and compositions for modulating expression of these polypeptides, and for identifying agents that modulate their expression. The genes encoding the polypeptides we have identified are listed in Tables 1 and 2, below. A first subset of the genes we have identified encodes polypeptides that are negative regulators of glucose transport. A second subset encodes positive regulators of glucose transport. Decreasing the expression or activity of negative regulators of glucose transport (e.g., via inhibition of gene expression with antisense or siRNA or with agents that inhibit the activity of the gene product) can result in increase glucose uptake, thereby lowering blood glucose levels. Increasing expression or activity of positive regulators (e.g., via overexpression of the gene product or via use of agents that increase the activity of the regulators) can also enhance insulin action, thereby promoting glucose uptake.

Negative Regulators of Glucose Transport

We have found that inhibiting expression of the genes listed in Table 1 potentiates insulin action by increasing insulin-stimulated glucose uptake. Potentiation of insulin action is beneficial, e.g., in controlling blood glucose action in vivo, e.g., in diabetic patients. Thus, inhibiting the expression or activity of these gene products can be beneficial in the treatment of conditions in which insulin activity or glucose transport is disregulated.

TABLE 1

Negative Regulators of Glucose Transport

| Gene or Gene Product Name (abbreviated) | Gene or Gene Product Name | GenBank ® Accession No.* | Comments |
| --- | --- | --- | --- |
| Pex13 | Peroxin 13 | BC023683 | Component of peroxisomal translocation machinery |

TABLE 1-continued

Negative Regulators of Glucose Transport

| Gene or Gene Product Name (abbreviated) | Gene or Gene Product Name | GenBank ® Accession No.* | Comments |
| --- | --- | --- | --- |
| Ar16ip2 | ADP-ribosylation factor-like 6 interacting protein | NM_178050 | |
| SOD1 | Superoxide dismutase 1 | BC057074 | Synonym: B430204E11Rik |
| FSP27 | Fat specific gene 27 | Mouse: NM_178373 Human: AY364640 | |
| Fzd4 | Frizzled homolog 4 | Mouse: NM_008055 Human: AB032417 | |
| Sycp3 | Synaphin 3 | Mouse: NM_011517 Human: NM_153694 | |
| Ptpra | Protein tyrosine phosphatase receptor type A | M36033 (NM_008980) | Phosphatase |
| Chuk (IKKα) | Conserved helix-loop-helix ubiquitous kinase | Mouse: NM_007700 Human: NM_001278 | Kinase |
| Map4k4 | Mitogen-activated protein kinase kinase kinase kinase 4 | Mouse: NM_008696 Human: NM_145686 | Kinase |
| Pctk1 | PCTAIRE-motif protein kinase 1 | Mouse: NM_011049 Human: X66363 | Kinase |
| Pctk3 | PCTAIRE-motif protein kinase 3 | Mouse: NM_008795 Human: NM_212502 | Kinase |
| Pftk1 | PFTAIRE protein kinase 1 | NM_011074 | Kinase |
| Mapk8-A (JNK1) | Mitogen activated protein kinase 8 | NM_016700 | Kinase |
| Mapk9 (JNK2) | Mitogen activated protein kinase 9 | NM_016961 | Kinase |
| Mark3 | MAP/microtubule affinity-regulating kinase 3 | NM_022801 | Kinase |
| IRAK1 | Interleukin-1 receptor-associated kinase 1 | NM_008363 | Kinase |
| Nme3 | Expressed in non-metastatic cells 3 | NM_019730 | Kinase |

*GenBank ® entries in this table refer to murine sequences unless otherwise noted.

Peroxin-13

Peroxin-13 (Pex13) is a component of the peroxisomal translocation machinery along with Peroxin-14 and Peroxin-17. Both N- and C-termini of Pex13 are oriented to the cytosol. Pex13 encodes an SH3-containing peroxisomal membrane protein required for the import of proteins into peroxisomes such as peroxin-14. In humans, mutations in PEX13 can disrupt peroxisome biogenesis and lead to peroxisomal metabolic dysfunction and neurodegenerative disease. Murine PEX13 spans 18 kb and consists of four exons. Pex13 transcripts were detected in all mouse tissues tested, with highest levels in liver and testis. The PEX13 open reading frame predicts a 44.5-kDa protein that displays 91% sequence identity to the human protein.

Fat Specific Gene 27

Fat Specific Gene 27 (FSP 27) encodes a protein of 27 kDa (Danesch et al., *J. Biol. Chem.*, 267(10):7185-93, 1992).

FSP27 encodes a domain that is found in caspase-activated (CAD) nuclease, which induces DNA fragmentation and chromatin condensation during apoptosis; and in the cell death activator proteins CIDE-A and CIDE-B, which are inhibitors of CAD nuclease. The two proteins interact through this domain (Enari et al., *Nature,* 391:43-50, 1998; Sakahira et al., *Nature,* 391:96-99, 1998).

A human homolog of mouse FSP27, CIDE-3 (cell-death-inducing DFF45-like effectors) has been identified (Liang et al., *Biochem J.,* 370:195-203, 2003). The nucleic acid sequence of CIDE-3 is found under GenBank® Acc. No. AY364640.

Frizzled Homolog 4

Members of the 'frizzled' (FZ) gene family encode 7-transmembrane domain proteins that are receptors for Wnt signaling proteins. The human FZD4 gene encodes a deduced 537-amino acid protein that has a cysteine-rich domain (CRD) in the N-terminal extracellular region, 2 cysteine residues in the second and third extracellular loops, 2 extracellular N-linked glycosylation sites, and the S/T-X-V motif in the C terminus (Kirikoshi et al., *Biophys. Res. Commun.,* 264: 955-961, 1999; see also GenBank® Acc. No. AB032417). Mutations in FZD4 have been linked with familial exudative vitreoretinopathy (FEVR), a hereditary ocular disorder characterized by a failure of peripheral retinal vascularization (Robitaille et al., *Nat Genet.,* 32(2):326-30, 2002).

Synaphin 3

Synaphin 3 (also known as Synaptonemal Complex Protein 3, or Sycp3) encodes a protein component of the synaptonemal complex. Humans heterozygous for a mutation in SYCP3 are azoospermic, indicating that the Sycp3 is essential for meiotic function in human spermatogenesis (Miyamoto et al., *Lancet,* 362(9397):1714-9, 2003).

Protein Tyrosine Phosphatase Receptor Type A

Protein Tyrosine Phosphatase Receptor Type A (Ptpra) is a tyrosine specific protein phosphatase. Although Ptpra has been implicated in insulin signaling in cultured cells, Ptpra-null mice reveal that the polypeptide is not essential for mediating the physiological action of insulin (Le et al., *Biochem. Biophys. Res. Commun.,* 314 (2):321-329, 2004).

Conserved Helix-Loop-Helix Ubiquitous Kinase

Conserved Helix-Loop-Helix Ubiquitous Kinase (Chuk; also known as I Kappa B Kinase α, or IKKα) is a serine/threonine kinase that is expressed in a broad array of tissues and exhibits a high degree of conservation across species. Chuk contains kinase, leucine zipper, and helix-loop-helix domains (Mercurio et al., *Science,* 278(5339):860-6, 1997). Phosphorylation of serine residues on the IKB proteins by kinases such as IKKα marks them for destruction via the ubiquitination pathway, thereby allowing activation of the NF-kappa-B complex.

Mitogen-activated Protein Kinase Kinase Kinase Kinase 4

Mitogen-activated Protein Kinase Kinase Kinase Kinase 4 (Map4k4; also known as NCK-interacting Kinase, or NIK; also referred to herein as Map4k4/NIK) is a serine/threonine kinase that regulates diverse signaling pathways and is essential for mammalian development (Xue et al., *Development,* 128(9):1559-1572, 2001). This kinase has been shown to specifically activate MAPK8/JNK. The activation of MAPK8 by Map4k4 is found to be inhibited by the dominant-negative mutants of MAP3K7/TAK1, MAP2K4/MKK4, and MAP2K7/MKK7, which suggests that this kinase may function through the MAP3K7-MAP2K4-MAP2K7 kinase cascade, and mediate the TNFα signaling pathway.

Exemplary nucleic acid and amino acid sequences for human Map4k4 are found under GenBank Nos. NM_145686 and NP_663719, respectively. The N-terminus of the human Map4k4 polypeptide has a catalytic kinase domain with 11 kinase subdomains (Yao et al., *J. Biol. Chem.,* 274: 2118-2125, 1999). Map4k4 shares 47% and 48% amino acid sequence identity to the catalytic domain of Hematopoietic Progenitor Kinase 1 (HPK1) and Germinal Center Kinase, GCK, respectively. Other polypeptides which have been shown to interact with human Map4k4 include: Caspase 8, Docking protein 1; guanylate binding protein 3; Integrin beta 1; Nck adaptor protein 1; Solute carrier family 9, isoform A1; RasGAP; solute carrier family 9 (sodium/hydrogen exchanger), member 1; and MEKK1.

PCTAIRE-1

PCTAIRE-1 (Pctk1) is a cyclin dependent kinase-related protein found in terminally differentiated cells in brain and testis. (Graeser et al., *J. Cell Sci.,* 115:3479-3490, 2002). Like cyclin dependent kinases, Pctk1 may play a role in cell cycle regulation (Myerson, *EMBO J.,* 11 (8):2909-17, 1992).

PCTAIRE-3

PCTAIRE-3 (Pctk3) is 65% homologous to Pctk1 and is expressed in brain, kidney and intestine (Okuda et al. *Oncogene,* 7(11):2249-58, 1992).

PFTAIRE Protein Kinase 1

PFTAIRE Protein Kinase 1 (Pftk1) is a cdk-related protein kinase and exhibits approximately 50% identity with Pctk3. Pftk1 is widely expressed in murine tissue and is though to play a role in meiosis and neuronal function (Besset et al., *Mol. Reprod. Dev.,* 50(1): 18-29, 1998).

Mitogen Activated Protein Kinase 9

Mitogen activated protein kinase 9 (Mapk9; also known as JNK2) can inhibit insulin signaling by stimulating phosphorylation of insulin receptor substrate 1 (Irs1) (Lee et al., *J. Biol. Chem.,* 278(5): 2896-902, 2003).

Positive Regulators of Glucose Transport

Increasing expression or activity of the genes listed in Table 2 can potentiate insulin action by increasing insulin-stimulated glucose uptake. As discussed for the negative regulators, above, potentiation of insulin action is beneficial, e.g., in controlling blood glucose action in vivo. Thus, increasing the expression or activity of these gene products can be beneficial in the treatment of conditions in which insulin activity or glucose transport is disregulated such as diabetes.

TABLE 2

Positive Regulators of Glucose Transport

| Gene or Gene Product Name (abbreviated) | Gene or Gene Product Name | GenBank ® Accession No.* | Comments |
|---|---|---|---|
| 9130022E05Rik | | AK078461 | |
| 2900045N06Rik | | NM_028385 | |
| 4930402E16Rik | | AK129472 | |
| 5730403B10Rik | | NM_025670 | |
| Abcf1 | ATP-binding cassette, sub-family F | BC063094 | |
| D11Ertd498 | | BC024811 | |
| D19Ertd703e | | AK018652 | |
| F830029L24Rik | | BC059190 | |
| G430055L02Rik | | BC015285 | |
| Crim1 | Cysteine-rich motor neuron 1 | XM_128751 | |
| Dvl1 | Dishevelled segment polarity protein homolog | U10115 | |

TABLE 2-continued

Positive Regulators of Glucose Transport

| Gene or Gene Product Name (abbreviated) | Gene or Gene Product Name | GenBank® Accession No.* | Comments |
|---|---|---|---|
| Lpin1 | Lipin | AF180471 | |
| Nsdh1 | NAD(P) dependent steroid dehydrogenase-like | NM_010941 | |
| Ilk | Integrin linked kinase | NM_010562 | Kinase |
| Pard6g | Par-6 partitioning defective 6 homolog gamma | NM_053117 | |

*GenBank® entries in this table refer to murine sequences unless otherwise noted.

9130022E05Rik

The gene product encoded by 9130022E05Rik, the nucleotide sequence of which can be found under GenBank® Acc. No. AK078461, exhibits homology to human regulatory solute carrier protein, family 1 (RSC1A1) and includes a putative ubiquitin associated (UBA) domain.

2900045N06Rik

2900045N06Rik (found under GenBank® Acc. No. NM_028385) encodes a putative SET methyl transferase domain and a putative ZnF_NFX transcriptional repressor domain.

4930402E16Rik

4930402E16Rik (found under GenBank® Acc. No. AK129472) encodes domains with homology to dimethylglycine dehydrogenase and glycine cleavage T-protein (GCV_T aminomethyl transferase) domains.

5730403B10Rik

The gene product encoded by 5730403B10Rik (found under GenBank® Acc. No. NM_025670) encodes a putative LPS-induced tumor necrosis factor alpha factor (LITAF) membrane associated motif, also known as PIG7.

ATP-Binding Cassette, Sub-Family F, Member 1

The ATP-binding Cassette, Sub-family F (GCN20), Member 1 (Abcf1) gene sequence is homologous to the human ABC50 sequence. Human ABC50 is an ABC family member that appears to lack the transmembrane domains typical of ABC transporters and may encode protein involved in translation of mRNA (Richard et al., *Genomics*, 53(2):137-45, 1998).

Cysteine-Rich Motor Neuron 1

The Cysteine-rich Motor Neuron 1 gene (CRIM1) encodes a transmembrane protein containing an insulin-like growth factor (IGF)-binding protein motif and multiple cysteine-rich repeats (Kolle et al., *Mech. Dev.*, 90(2): 181-193, 2000).

Dishevelled Segment Polarity Protein Homolog

The Dishevelled Segment Polarity Protein Homolog gene product (Dvl-1) has been implicated in microtubule assembly (Krylova et al., *J. Cell Biol.*, 151(1):83-94, 2000) and may regulate neurite outgrowth in conjunction with Wnt proteins (Kishida et al., *Mol Cell Biol.*, 24(10):4487-501, 2004).

Lipin

The Lipin gene product (Lpin1) is required for induction of adipogenic gene transcription in mice, and mutations in the gene cause lipodystrophy in the fatty liver dystrophy (fld) mouse (Phan et al., *J. Biol. Chem.*, 279(28):29558-64, 2004).

NAD(P)H Steroid Dehydrogenase-Like Gene

NAD(P)H Steroid Dehydrogenase-like Gene (NSDHL) encodes a sterol dehydrogenase or decarboxylase involved in post-squalene cholesterol biosynthesis. Mutations in the human gene are associated with the human CHILD syndrome (congenital hemidysplasia with ichthyosiform nevus and limb defects) (Caldas and Herman, *Hum. Mol., Genet.*, 12(22):2981-2991, 2003). NSDHL is localized in the endoplasmic reticulum and associates with lipid droplets (Caldas and Herman, supra).

Integrin Linked Kinase

Integrin Linked Kinase (Ilk) is a component of focal adhesions and binds to the cytoplasmic tail of integrins, modulating actin rearrangements at integrin adhesion sites (Sakai et al., *Genes Dev.*, 17(7): 926-920, 2003).

Par-6 Partitioning Defective 6 Homolog Gamma

Par-6 Partitioning Defective 6 Homolog Gamma (Pard6g) are similar to the *C. elegans* PDZ-domain protein PAR-6. Par6 is implicated in the formation of tight junctions at epithelial cell-cell contacts (Joberty et al., *Nat. Cell. Biol.*, 2(8): 531-539, 2000).

Screening Assays

Provided herein are methods for identifying modulators, i.e., candidate agents or reagents, of expression or activity of a glucose transport-related nucleic acid or polypeptide. Such candidate agents or reagents include polypeptides, oligonucleotides, peptidomimetics, carbohydrates, or small molecules such as small organic or inorganic molecules (e.g., non-nucleic acid small organic chemical compounds) that modulate expression (protein or mRNA) or activity of one or more glucose transport-related polypeptides or nucleic acids. In general, screening assays involve assaying the effect of a test agent on expression or activity of a glucose transport-related nucleic acid or polypeptide in a test sample (i.e., a sample containing the glucose transport-related nucleic acid or polypeptide). Expression or activity in the presence of the test compound or agent is compared to expression or activity in a control sample (i.e., a sample containing a glucose transport-related polypeptide that was incubated under the same conditions, but without the test compound). A change in the expression or activity of the glucose transport-related nucleic acid or polypeptide in the test sample compared to the control indicates that the test agent or compound modulates expression or activity of the glucose transport-related nucleic acid or polypeptide and is a candidate agent.

In one embodiment, the invention provides assays for screening test agents that bind to or modulate the activity of a glucose transport-related polypeptide or nucleic acid encoding the polypeptide or biologically active portion thereof. The test compounds to be screened, can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer, or small molecule libraries of compounds (Lam, *Anticancer Drug Des.*, 12:145, 1997).

Examples of methods for the synthesis of molecular libraries can be found in the literature, for example in: DeWitt et al., *Proc. Natl. Acad. Sci. USA*, 90:6909, 1993; Erb et al., *Proc. Natl. Acad. Sci. USA*, 91:11422, 1994; Zuckermann et al., *J. Med. Chem.* 37:2678, 1994; Cho et al., *Science* 261:1303, 1993; Carrell et al., *Angew. Chem. Int. Ed. Engl.* 33:2059, 1994; Carell et al., *Angew. Chem. Int. Ed. Engl.*, 33:2061, 1994; and Gallop et al., *J Med. Chem.*, 37:1233, 1994.

Libraries of compounds may be presented in solution (e.g., Houghten, *Bio/Techniques*, 13:412-421, 1992), or on beads (Lam, *Nature*, 354:82-84, 1991), chips (Fodor, *Nature* 364:

555-556, 1993), bacteria (U.S. Pat. No. 5,223,409), spores (U.S. Pat. Nos. 5,571,698; 5,403,484; and 5,223,409), plasmids (Cull et al., *Proc. Natl. Acad. Sci. USA,* 89:1865-1869, 1992) or phage (Scott and Smith, *Science,* 249:386-390, 1990; Devlin, *Science,* 249:404-406, 1990; Cwirla et al., *Proc. Natl. Acad. Sci. USA,* 87:6378-6382, 1990; and Felici, *J. Mol. Biol.,* 222:301-310, 1991).

In one embodiment, the assay is a cell-based assay in which a cell expressing a glucose transport-related polypeptide (e.g., a gene product of a gene Table 1 or 2), or a biologically active portion thereof, on the cell surface is contacted with a test compound. The ability of the test compound to bind to the polypeptide is then determined. The cell, for example, can be a yeast cell or a cell of mammalian origin. The ability of the test compound to bind to the polypeptide can be determined, for example, by coupling the test compound with a radioisotope or enzymatic label such that binding of the test compound to the polypeptide or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting.

Alternatively, test compounds can be enzymatically labeled with, for example, horseradish peroxidase, alkaline phosphatase, or luciferase, and the enzymatic label detected by determination of conversion of an appropriate substrate to product. In one embodiment, the assay includes contacting a cell that expresses a membrane-bound form of the glucose transport-related polypeptide, or a biologically active portion thereof, on the cell surface with a known compound that binds to the polypeptide to form an assay mixture, contacting the assay mixture with a test compound, and determining the ability of the test compound to interact with the polypeptide, e.g., by observing whether the test compound preferentially binds to the polypeptide or a biologically active portion thereof as compared to the known compound.

In another embodiment, an assay is a cell-based assay that includes contacting a cell expressing a membrane-bound form of a glucose transport-related polypeptide, or a biologically active portion thereof, on the cell surface with a test compound and determining the ability of the test compound to modulate (e.g., stimulate or inhibit) the activity of the polypeptide or biologically active portion thereof. The ability of the test compound to modulate the activity of the polypeptide or a biologically active portion thereof can be determined, for example, by monitoring the ability of the polypeptide to bind to or interact with a target molecule.

The ability of a polypeptide or nucleic acid to bind to or interact with a target molecule can be determined by one of the direct binding methods described herein. As used herein, a "target molecule" is a molecule with which a selected polypeptide or nucleic acid (e.g., a gene or polypeptide encoded by a gene of Table 1 or Table 2, or a homolog thereof) binds or interacts with in nature, for example, a molecule on the surface of a cell that expresses the selected protein, a molecule on the surface of a second cell, a molecule in the extracellular milieu, a molecule associated with the internal surface of a cell membrane, or a cytoplasmic molecule. A target molecule can be a glucose transport related polypeptide or nucleic acid or some other polypeptide, protein, or nucleic acid. For example, a target molecule can be a component of a signal transduction pathway that facilitates transduction of an extracellular signal (e.g., a signal generated by binding of a compound to a glucose transport-related polypeptide) through the cell membrane and into the cell or a second intercellular protein that has catalytic activity, or a protein that facilitates the association of downstream signaling molecules with a glucose transport-related polypeptide.

The ability of a polypeptide to bind to or interact with a target molecule can also be determined. For example, the activity of the target molecule can be determined by detecting induction of a cellular second messenger of the target (e.g., intracellular $Ca^{2+}$, diacylglycerol, or IP3), detecting catalytic/enzymatic activity of the target on an appropriate substrate (e.g., detecting kinase activity where the glucose transport-related polypeptide is a kinase), detecting the induction of a reporter gene (e.g., a regulatory element that is responsive to a glucose transport-related polypeptide operably linked to a nucleic acid encoding a detectable marker, e.g., luciferase), or detecting a cellular response, for example, cellular differentiation, or cell proliferation. When the target molecule is a nucleic acid, the compound can be, e.g., a ribozyme or antisense molecule.

In yet another embodiment, an assay as described herein includes contacting a glucose transport-related polypeptide (e.g., a gene product of a gene of Table 1 or 2) or nucleic acid encoding the polypeptide, or biologically active portion thereof, with a test compound and determining the ability of the test compound to bind to the polypeptide or biologically active portion thereof. Binding of the test compound to the polypeptide can be determined either directly or indirectly as described above. In one embodiment, the assay includes contacting the polypeptide or biologically active portion thereof with a known compound that specifically binds the polypeptide to form an assay mixture, contacting the assay mixture with a test compound, and determining the ability of the test compound to interact with the polypeptide (e.g., its ability to compete with binding of the known compound). One can evaluate the ability of the test compound to interact with the polypeptide by determining whether the test compound can preferentially bind to the polypeptide or biologically active portion thereof as compared to the known compound. When the test compound is targeted to a nucleic acid, the binding of the test compound to the nucleic acid can be tested, e.g., by binding, by fragmentation of the nucleic acid (as when the test compound is a ribozyme), or by inhibition of transcription or translation in the presence of the test compound.

In another embodiment, an assay is a cell-free assay that includes contacting a glucose transport-related polypeptide biologically active portion thereof with a test compound and determining the ability of the test compound to modulate (e.g., stimulate or inhibit) the activity of the polypeptide or biologically active portion thereof. For example, determining the ability of the test compound to modulate the activity of the polypeptide can be accomplished by determining the ability of the polypeptide to modify a target molecule. Such methods can, alternatively, measure the catalytic/enzymatic activity of the target molecule on an appropriate substrate. A number of the genes in Table 1 and 2 encode kinases. For the products of these genes, one can utilize kinase assays to identify an agent that modulates the activity of the gene product. In general, modulation of an activity of the polypeptide (or a biologically portion thereof), by a kinase assay or another type of assay, is determined by comparing the activity in the absence of the test compound to the activity in the presence of the test compound. In general, modulation of an activity of the polypeptide (or a biologically portion thereof), by a kinase assay or another type of assay, is determined by comparing the activity in the absence of the test compound to the activity in the presence of the test compound. For example, to determine the activity of a kinase (e.g., a kinase listed in Table 1 or Table 2) in the presence of a test compound, any standard assay for protein phosphorylation can be carried out. One can use a natural substrate of the kinase or another protein or peptide that the kinase phosphorylates. Assays for kinase activity can also be carried out with biologically active fragments of the kinase (e.g., a fragment that retains catalytic activity).

In yet another embodiment, the cell-free assay includes contacting a glucose transport-related polypeptide or nucleic acid encoding the polypeptide, or biologically active portion thereof, with a known compound that binds to the polypeptide to form an assay mixture, contacting the assay mixture with a test compound, and determining the ability of the test compound to interact with the polypeptide or nucleic acid by assaying the ability of the polypeptide or nucleic acid to preferentially bind to or modulate the activity of a target molecule (e.g., a target molecule that is a natural substrate or binding partner of the polypeptide).

Cell-free assays are amenable to use of either a soluble form or a membrane-bound form of a polypeptide (if the polypeptide is a membrane-containing polypeptide. In the case of cell-free assays comprising a membrane-bound form of the polypeptide, it may be desirable to utilize a solubilizing agent such that the membrane-bound form of the polypeptide is maintained in solution. Examples of such solubilizing agents include non-ionic detergents such as n-octylglucoside, n-dodecylglucoside, n-octylmaltoside, octanoyl-N-methyl-glucamide, decanoyl-N-methylglucamide, Triton X-100®, Triton X-114®, Thesit, Isotridecypoly(ethylene glycol ether) n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), and N-dodecyl-N,N-dimethyl-3-ammonio-1-propane sulfonate.

In certain embodiments of the new assay methods, it may be desirable to immobilize either the glucose transport-related polypeptide or its target molecule to facilitate separation of complexed from uncomplexed forms of one or both of the proteins, as well as to automate the assay. Binding of a test compound to the polypeptide, or interaction of the polypeptide with a target molecule in the presence and absence of a test agent, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase fusion proteins or glutathione-S-transferase fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or a glucose-transport-related polypeptide, and the mixture incubated under conditions conducive to complex formation (e.g., at physiological conditions for salt and pH). Following incubation, the beads or microtiter plate wells are washed to remove any unbound components and complex formation is measured either directly or indirectly, for example, as described above. Alternatively, the complexes can be dissociated from the matrix, and the level of binding or activity of the polypeptide can be determined using standard techniques.

Other techniques for immobilizing proteins on matrices can also be used in the screening assays. For example, either the glucose transport-related polypeptide or its target molecule can be immobilized utilizing conjugation of biotin and streptavidin. Biotinylated polypeptides or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical).

Alternatively, antibodies reactive with the polypeptide or target molecules but which do not interfere with binding of the glucose transport-related polypeptide to its target molecule can be derivatized to the wells of the plate, and unbound target or polypeptide trapped in the wells by antibody conjugation. Methods for detecting such complexes such as GST-immobilized complexes, include immunodetection of complexes using antibodies reactive with the polypeptide or target molecule, as well as enzyme-linked assays which rely on detecting an enzymatic activity associated with the polypeptide or target molecule.

In another embodiment, modulators of expression of a polypeptide are identified in a method in which a cell is contacted with a test agent or compound and the expression of the selected mRNA or protein (e.g., the mRNA or protein corresponding to a glucose transport-related polypeptide or gene encoding the polypeptide, e.g., in Table 1 or 2) in the cell is determined. The level of expression of the selected mRNA or protein in the presence of the test agent is compared to the level of expression of the selected mRNA or protein in the absence of the test agent. The test agent can then be identified as a modulator of expression of the polypeptide (i.e., a candidate compound) based on this comparison. For example, when expression of the selected mRNA or protein is greater (statistically significantly greater) in the presence of the test agent than in its absence, the test agent is identified as a candidate agent that is a stimulator of the selected mRNA or protein expression. Alternatively, when expression of the selected mRNA or protein is less (statistically significantly less) in the presence of the test agent than in its absence, the test agent is identified as a candidate agent that is an inhibitor of the selected mRNA or protein expression. The level of the selected mRNA or protein expression in the cells can be determined by methods described herein.

In yet another aspect, a glucose transport-related polypeptide can be used as a "bait protein" in a two-hybrid assay or three hybrid assay (see, e.g., U.S. Pat. No. 5,283,317; Zervos et al., *Cell,* 72:223-232, 1993; Madura et al., *J. Biol. Chem.* 268:12046-12054, 1993; Bartel et al., *Bio/Techniques* 14:920-924, 1993; Iwabuchi et al., *Oncogene* 8:1693-1696, 1993; and PCT Publication No. WO 94/10300), to identify other proteins that bind to or interact with the glucose transport-related polypeptide and modulate activity of the polypeptide. Such binding proteins are also likely to be involved in the propagation of signals by the glucose transport-related polypeptide as, for example, downstream elements of the signaling pathway involving glucose transport.

Isolating Homologous Sequences from Other Species

The human homologs of glucose-transport related genes and their products are useful for various embodiments of the present invention including for screening modulators and diagnosing of glucose transport-related disorders such as type II diabetes. Homologs have already been identified for certain genes. In those cases where a human homolog is not identified, several approaches can be used to identify such genes. These methods include low stringency hybridization screens of human libraries with a mouse glucose transport-related nucleic acid sequence, polymerase chain reactions (PCR) of human DNA sequence primed with degenerate oligonucleotides derived from a mouse glucose transport-related gene, two-hybrid screens, and database screens for homologous sequences.

Antisense Nucleic Acids

Agents to modulate the expression of the glucose transport-related polypeptides described herein include antisense nucleic acid molecules, i.e., nucleic acid molecules whose nucleotide sequence is complementary to all or part of an mRNA based on the sequence of a gene encoding glucose transport-related polypeptide (e.g., based on a sequence of a gene of Tables 1 or 2). An antisense nucleic acid molecule can be antisense to all or part of a non-coding region of the coding strand of a nucleotide sequence encoding the glucose transport-related polypeptide. Non-coding regions ("5' and 3' untranslated regions") are the 5' and 3' sequences that flank the coding region in a gene and are not translated into amino acids.

Based upon the sequences disclosed herein, one of skill in the art can easily choose and synthesize any of a number of appropriate antisense molecules to target a gene described herein. For example, a "gene walk" comprising a series of oligonucleotides of 15-30 nucleotides spanning the length of a nucleic acid described in Table 1 can be prepared, followed by testing for inhibition of expression of the gene. Optionally, gaps of 5-10 nucleotides can be left between the oligonucleotides to reduce the number of oligonucleotides synthesized and tested.

An antisense oligonucleotide can be, for example, about 5, 10, 15, 20, 25, 30, 35, 40, 45, or 50 nucleotides or more in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules described herein can be prepared in vitro and administered to an animal, e.g., a mammal, e.g., a human patient. Alternatively, they can be generated in situ such that they hybridize with or bind to cellular mRNA and/or genomic DNA encoding a selected polypeptide of the invention to thereby inhibit expression, e.g., by inhibiting transcription and/or translation. The hybridization can be by conventional nucleotide complementarities to form a stable duplex, or, for example, in the case of an antisense nucleic acid molecule that binds to DNA duplexes, through specific interactions in the major groove of the double helix. An example of a route of administration of antisense nucleic acid molecules includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. For example, to achieve sufficient intracellular concentrations of the antisense molecules, vector constructs can be used in which the antisense nucleic acid molecule is placed under the control of a strong pol II or pol III promoter.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al., *Nucleic Acids Res.* 15:6625-6641, 1987). The antisense nucleic acid molecule can also comprise a 2'-o-methylribonucleotide (Inoue et al., *Nucleic Acids Res.*, 15:6131-6148, 1987) or a chimeric RNA-DNA analog (Inoue et al., *FEBS Lett.*, 215: 327-330, 1987).

Antisense molecules that are complementary to all or part of a glucose transport-related gene are also useful for assaying expression of such genes using hybridization methods known in the art. For example, the antisense molecule is labeled (e.g., with a radioactive molecule) and an excess amount of the labeled antisense molecule is hybridized to an RNA sample. Unhybridized labeled antisense molecule is removed (e.g., by washing) and the amount of hybridized antisense molecule measured. The amount of hybridized molecule is measured and used to calculate the amount of expression of the glucose transport-related gene. In general, antisense molecules used for this purpose can hybridize to a sequence from a glucose transport-related gene under high stringency conditions such as those described herein. When the RNA sample is first used to synthesize cDNA, a sense molecule can be used. It is also possible to use a double-stranded molecule in such assays as long as the double-stranded molecule is adequately denatured prior to hybridization.

Ribozymes

Also provided are ribozymes that have specificity for sequences encoding the glucose transport-related polypeptides described herein (e.g., for sequences of the genes in Table 1 or 2). Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haselhoff and Gerlach, *Nature*, 334: 585-591, 1988)) can be used to catalytically cleave mRNA transcripts to thereby inhibit translation of the protein encoded by the mRNA. A ribozyme having specificity for a nucleic acid molecule of the invention can be designed based upon the nucleotide sequence of a cDNA disclosed herein. For example, a derivative of a *Tetrahymena* L-19 IVS RNA can be constructed in which the nucleotide sequence of the active site is complementary to the nucleotide sequence to be cleaved in a glucose transport-related mRNA (Cech et al. U.S. Pat. No. 4,987,071; and Cech et al., U.S. Pat. No. 5,116,742). Alternatively, an mRNA encoding a polypeptide of the invention can be used to select a catalytic RNA having a specific ribonuclease activity from a pool of RNA molecules. See, e.g., Bartel and Szostak, *Science,* 261:1411-1418, 1993.

Also provided herein are nucleic acid molecules that form triple helical structures. For example, expression of a glucose transport-related polypeptide can be inhibited by targeting nucleotide sequences complementary to the regulatory region of the gene encoding the polypeptide (e.g., the promoter and/or enhancer) to form triple helical structures that prevent transcription of the gene in target cells. See generally Helene, *Anticancer Drug Des.* 6(6):569-84, 1991; Helene, *Ann. N.Y. Acad. Sci.,* 660:27-36, 1992; and Maher, *Bioassays,* 14(12): 807-15, 1992.

In various embodiments, nucleic acid molecules (e.g., nucleic acid molecules used to modulate expression of a glucose transport-related polypeptide) can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al., *Bioorganic & Medicinal Chem.,* 4(1): 5-23, 1996). Peptide nucleic acids (PNAs) are nucleic acid mimics, e.g., DNA mimics, in which the deoxyribose phosphate backbone is replaced by a pseudopeptide backbone and only the four natural nucleobases are retained. The neutral backbone of PNAs allows for specific hybridization to DNA and RNA under conditions of low ionic strength. The synthesis of PNA oligomers can be performed using standard solid phase peptide synthesis protocols, e.g., as described in Hyrup et al., 1996, supra; Perry-O'Keefe et al., *Proc. Natl. Acad. Sci. USA,* 93: 14670-675, 1996.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup, 1996, supra; or as probes or primers for DNA sequence and hybridization (Hyrup, 1996, supra; Perry-O'Keefe et al., *Proc. Natl. Acad. Sci. USA,* 93: 14670-675, 1996).

PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup, 1996, supra, and Finn et al., *Nucleic Acids Res.,* 24:3357-63, 1996. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., *Nucleic Acids Res.,* 17:5973-88, 1989). PNA monomers are then coupled in a stepwise manner to produce a chimeric molecule with a 5' PNA segment and a 3' DNA segment (Finn et al., *Nucleic Acids Res.,* 24:3357-63, 1996). Alternatively, chimeric molecules can be synthesized with a 5' DNA segment and a 3' PNA segment (Peterser et al., *Bioorganic Med. Chem. Lett.,* 5:1119-11124, 1975).

In some embodiments, the oligonucleotide includes other appended groups such as peptides (e.g., for targeting host cell receptors in vivo), or agents facilitating transport across the cell membrane (see, e.g., Letsinger et al., *Proc. Natl. Acad. Sci. USA,* 86:6553-6556, 1989; Lemaitre et al., *Proc. Natl. Acad. Sci. USA,* 84:648-652, 1989; WO 88/09810) or the blood-brain barrier (see, e.g., WO 89/10134). In addition, oligonucleotides can be modified with hybridization-triggered cleavage agents (see, e.g., Krol et al., *Bio/Techniques,* 6:958-976, 1988) or intercalating agents (see, e.g., Zon, *Pharm. Res.,* 5:539-549, 1988). To this end, the oligonucleotide may be conjugated to another molecule, e.g., a peptide, hybridization triggered cross-linking agent, transport agent, hybridization-triggered cleavage agent, etc.

siRNA

Another means by which expression of glucose transport-related polypeptides can be inhibited is by RNA interference (RNAi). RNAi is a process in which mRNA is degraded in host cells. To inhibit an mRNA, double-stranded RNA (dsRNA) corresponding to a portion of the gene to be silenced (e.g., a gene encoding a glucose transport-related polypeptide, e.g., a gene of Table 1) is introduced into a cell. The dsRNA is digested into 21-23 nucleotide-long duplexes called short interfering RNAs (or siRNAs), which bind to a nuclease complex to form what is known as the RNA-induced silencing complex (or RISC). The RISC targets the homologous transcript by base pairing interactions between one of the siRNA strands and the endogenous mRNA. It then cleaves the mRNA about 12 nucleotides from the 3' terminus of the siRNA (see Sharp et al., *Genes Dev.* 15:485-490, 2001, and Hammond et al., *Nature Rev. Gen.,* 2:110-119, 2001).

RNA-mediated gene silencing can be induced in mammalian cells in many ways, e.g., by enforcing endogenous expression of RNA hairpins (see Paddison et al., *Proc. Natl. Acad. Sci. USA,* 99:1443-1448, 2002) or, as noted above, by transfection of small (21-23 nt) dsRNA (reviewed in Caplen, *Trends in Biotech.,* 20:49-51, 2002). Methods for modulating gene expression with RNAi are described, e.g., in U.S. Pat. No. 6,506,559 and U.S. Pat. Pub. No. 20030056235, which are hereby incorporated by reference.

Standard molecular biology techniques can be used to generate siRNAs. Short interfering RNAs can be chemically synthesized, recombinantly produced, e.g., by expressing RNA from a template DNA, such as a plasmid, or obtained from commercial vendors such as Dharmacon. The RNA used to mediate RNAi can include synthetic or modified nucleotides, such as phosphorothioate nucleotides. Methods of transfecting cells with siRNA or with plasmids engineered to make siRNA are routine in the art.

The siRNA molecules used to modulate expression of a glucose transport-related polypeptide can vary in a number of ways. For example, they can include a 3' hydroxyl group and strands of 21, 22, or 23 consecutive nucleotides. They can be blunt ended or include an overhanging end at either the 3' end, the 5' end, or both ends. For example, at least one strand of the RNA molecule can have a 3' overhang from about 1 to about 6 nucleotides (e.g., 1-5, 1-3, 2-4 or 3-5 nucleotides (whether pyrimidine or purine nucleotides) in length. Where both strands include an overhang, the length of the overhangs may be the same or different for each strand.

To further enhance the stability of the RNA duplexes, the 3' overhangs can be stabilized against degradation (by, e.g., including purine nucleotides, such as adenosine or guanosine nucleotides or replacing pyrimidine nucleotides by modified analogues (e.g., substitution of uridine 2 nucleotide 3' overhangs by 2'-deoxythymidine is tolerated and does not affect the efficiency of RNAi). Any siRNA can be used in the methods of modulating a glucose transport-related polypeptide, provided it has sufficient homology to the target of interest. There is no upper limit on the length of the siRNA that can be used (e.g., the siRNA can range from about 21 base pairs of the gene to the full length of the gene or more (e.g., 50-100, 100-250, 250-500, 500-1000, or over 1000 base pairs).

Isolated Polypeptides

Isolated polypeptides encoded by the glucose transport-related genes described herein are also provided. These polypeptides can be used, e.g., as immunogens to raise antibodies, in screening methods, or in methods of treating subject, e.g., by administration of the polypeptides. Methods are well known in the art for predicting the translation products of the nucleic acids (e.g., using computer programs that provide the predicted polypeptide sequences and direction as to which of the three reading frames is the open reading frame of the sequence). These polypeptide sequences can then be produced either biologically (e.g., by positioning the nucleic acid sequence that encodes them in-frame in an expression vector transfected into a compatible expression system) or chemically using methods known in the art. The entire polypeptide or a fragment thereof can be used in a method of treatment or to produce an antibody, e.g., that is useful in a screening assay.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as "contaminating protein"). In general, when the protein or biologically active portion thereof is recombinantly produced, it is also substantially free of culture medium, i.e., culture medium represents less than about 20%, 10%, or 5% of the volume of the protein preparation. In general, when the protein is produced by chemical synthesis, it is substantially free of chemical precursors or other chemicals, i.e., it is separated from chemical precursors or other chemicals that are involved in the synthesis of the protein. Accordingly such preparations of the protein have less than about 30%, 20%, 10%, or 5% (by dry weight) of chemical precursors or compounds other than the polypeptide of interest.

Expression of proteins and polypeptides can be assayed to determine the amount of expression. Methods for assaying protein expression are known in the art and include Western blot, immunoprecipitation, and radioimmunoassay.

Biologically active portions of a glucose transport-related polypeptide include polypeptides comprising amino acid sequences sufficiently identical to or derived from the amino acid sequence of the protein, which include fewer amino acids than the full length protein, and exhibit at least one activity of the corresponding full-length protein. Typically, biologically active portions comprise a domain or motif with at least one activity of the corresponding protein. A biologically active portion of a polypeptide can be, for example, 10, 25, 50, 100, or more amino acids in length. Moreover, biologically active portions, in which other regions of a given protein are deleted, can be prepared by recombinant techniques and evaluated for one or more of the functional activities of the native form of a polypeptide. These short polypeptides can be used in treatments to competitively inhibit activity of the gene products of the genes listed in Tables 1 and 2.

In some embodiments, glucose transport-related polypeptides have the predicted amino acid sequence encoded by a gene selected from the genes in Tables 1 and 2. Other useful proteins are substantially identical (e.g., at least about 45%, preferably 55%, 65%, 75%, 85%, 95%, or 99%) to the predicted amino acid sequence of a polypeptide encoded by a gene in Tables 1 and 2, and (a) retain the functional activity of the protein of the corresponding naturally-occurring protein yet differ in amino acid sequence due to natural allelic variation or mutagenesis, or (b) exhibit an altered functional activity (e.g., as a dominant negative) where desired.

The comparison of sequences and determination of percent identity between two sequences is accomplished using a mathematical algorithm. The percent identity between two amino acid sequences is determined using the Needleman and Wunsch ((1970) J. Mol. Biol. 48:444-453) algorithm, which has been incorporated into the GAP program in the GCG software package (available on the internet at the following address: gcg.com), using either a Blossum 62 matrix or a PAM250 matrix, and a gap weight of 16 and a length weight of 1. The percent identity between two nucleotide sequences is determined using the GAP program in the GCG software package (available on the internet at the following address: gcg.com), using a NWSgapdna.CMP matrix and a gap weight of 40 and a length weight of 1.

In general, percent identity between amino acid sequences referred to herein is determined using the BLAST 2.0 program, which is available to the public on the world wide web at the following address: ncbi.nlm.nih.gov/BLAST. Sequence comparison is performed using an ungapped alignment and using the default parameters (Blossum 62 matrix, gap existence cost of 11, per residue gap cost of 1, and a lambda ratio of 0.85). The mathematical algorithm used in BLAST programs is described in Altschul et al., Nucleic Acids Research 25:3389-3402, 1997.

Also provided herein are chimeric or fusion proteins. As used herein, a "chimeric protein" or "fusion protein" comprises all or part (e.g., a biologically active portion) of a glucose transport-related polypeptide operably linked to a heterologous polypeptide (i.e., a polypeptide other than the glucose transport-related polypeptide). In the context of a fusion protein, the term "operably linked" is intended to indicate that the polypeptide and the heterologous polypeptide are fused in-frame to each other. The heterologous polypeptide can be fused to the N-terminus or C-terminus of the glucose transport-related polypeptide.

One useful fusion protein is a GST fusion protein in which the glucose transport-related polypeptide is fused to the C-terminus of GST sequences. Such fusion proteins can facilitate the purification of a recombinant glucose transport-related polypeptide.

In another embodiment, the fusion protein contains a heterologous signal sequence at its N-terminus. For example, the native signal sequence of a glucose transport-related polypeptide can be removed and replaced with a signal sequence from another protein. For example, the gp67 secretory sequence of the baculovirus envelope protein can be used as a heterologous signal sequence (*Current Protocols in Molecular Biology*, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., eds., *Molecular Cloning: A Laboratory Manual. 2nd ed.*, Cold Spring Harbor Laboratory, Cold Spring Harbor Laboratory Press, Cold Spring Harbor, N.Y., 1989) and the protein A secretory signal (Pharmacia Biotech; Piscataway, N.J.).

In yet another embodiment, the fusion protein is an immunoglobulin fusion protein in which all or part of a glucose transport-related polypeptide is fused to sequences derived from a member of the immunoglobulin protein family. The immunoglobulin fusion proteins can be incorporated into pharmaceutical compositions and administered to a subject to inhibit an interaction between a ligand (soluble or membrane-bound) and a protein on the surface of a cell (receptor), to thereby suppress signal transduction in vivo. The immunoglobulin fusion protein can be used to affect the bioavailability of a cognate ligand of a glucose transport-related polypeptide. Inhibition of ligand/receptor interaction may be useful therapeutically, both for treating proliferative and differentiative disorders and for modulating (e.g., promoting or inhibiting) cell survival. Moreover, the immunoglobulin fusion proteins can be used as immunogens to produce antibodies directed against a glucose transport-related polypeptide in a subject, to purify ligands and in screening assays to identify molecules that inhibit the interaction of receptors with ligands.

Chimeric and fusion glucose transport-related polypeptides can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence. Moreover, many expression vectors are commercially available that already encode a fusion moiety (e.g., a GST polypeptide). A nucleic acid encoding a glucose transport-related polypeptide can be cloned into such an expression vector such that the fusion moiety is linked in-frame to the polypeptide.

A signal sequence of a polypeptide can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the described polypeptides having a signal sequence, as well as to the signal sequence itself and to the polypeptide in the absence of the signal sequence (i.e., the cleavage products), are provided herein. In one embodiment, a nucleic acid sequence encoding a signal sequence can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by methods known in the art. Alternatively, the signal sequence can be linked to the protein of interest using a sequence which facilitates purification, such as with a GST domain.

Also provided are variants of the glucose transport-related polypeptides. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Antibodies

An isolated glucose transport-related polypeptide, or a fragment thereof, can be used as an immunogen to generate antibodies using standard techniques for polyclonal and monoclonal antibody preparation. The full-length polypeptide or protein can be used or, alternatively, antigenic peptide fragments can be used as immunogens. The antigenic peptide of a protein comprises at least 8 (e.g., 10, 15, 20, or 30) amino acid residues of the amino acid sequence of a glucose transport-related polypeptide, e.g., encoded by a gene in Table 1 or Table 2, and encompasses an epitope of the protein such that an antibody raised against the peptide forms a specific immune complex with the protein.

An immunogen typically is used to prepare antibodies by immunizing a suitable subject, (e.g., rabbit, goat, mouse or other mammal). An appropriate immunogenic preparation can contain, for example, a recombinantly expressed or a chemically synthesized polypeptide. The preparation can further include an adjuvant, such as Freund's complete or incomplete adjuvant, or similar immunostimulatory agent.

Polyclonal antibodies can be prepared as described above by immunizing a suitable subject with a glucose transport-related polypeptide as an immunogen. The antibody titer in the immunized subject can be monitored over time by standard techniques, such as with an enzyme linked immunosorbent assay (ELISA) using immobilized polypeptide. If desired, the antibody molecules can be isolated from the mammal (e.g., from the blood) and further purified by well-known techniques, such as protein A chromatography to obtain the IgG fraction. At an appropriate time after immunization, e.g., when the specific antibody titers are highest, antibody-producing cells can be obtained from the subject and used to prepare monoclonal antibodies by standard techniques, such as the hybridoma technique originally described by Kohler and Milstein, *Nature* 256:495-497, 1975, the human B cell hybridoma technique (Kozbor et al., *Immunol. Today* 4:72, 1983), the EBV-hybridoma technique (Cole et al., *Monoclonal Antibodies and Cancer Therapy*, Alan R. Liss, Inc., pp. 77-96, 1985) or trioma techniques. The technology for producing hybridomas is well known (see generally *Current Protocols in Immunology*, 1994, Coligan et al. (eds.) John Wiley & Sons, Inc., New York, N.Y.). Hybridoma cells producing a monoclonal antibody are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against a polypeptide can be identified and isolated by screening a recombinant combinatorial immunoglobulin library (e.g., an antibody phage display library) with the polypeptide of interest. Kits for generating and screening phage display libraries are commercially available (e.g., the Pharmacia *Recombinant*

*Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, U.S. Pat. No. 5,223,409; WO 92/18619; WO 91/17271; WO 92/20791; WO 92/15679; WO 93/01288; WO 92/01047; WO 92/09690; WO 90/02809; Fuchs et al., *Bio/Technology* 9:1370-1372, 1991; Hay et al., *Hum. Antibod. Hybridomas* 3:81-85, 1992; Huse et al., *Science* 246:1275-1281, 1989; Griffiths et al., *EMBO J.* 12:725-734, 1993.

Additionally, recombinant antibodies, such as chimeric and humanized monoclonal antibodies, comprising both human and non-human portions, which can be made using standard recombinant DNA techniques, are provided herein. Such chimeric and humanized monoclonal antibodies can be produced by recombinant DNA techniques known in the art, for example using methods described in WO 87/02671; European Patent Application 184,187; European Patent Application 171,496; European Patent Application 173,494; WO 86/01533; U.S. Pat. No. 4,816,567; European Patent Application 125,023; Better et al., *Science,* 240:1041-1043, 1988; Liu et al., *Proc. Natl. Acad. Sci. USA* 84:3439-3443, 1987; Liu et al., *J. Immunol.,* 139:3521-3526, 1987; Sun et al., *Proc. Natl. Acad. Sci. USA,* 84:214-218, 1987; Nishimura et al., *Canc. Res.* 47:999-1005, 1987; Wood et al., *Nature,* 314:446-449, 1985; and Shaw et al., *J. Natl. Cancer Inst.,* 80:1553-1559, 1988); Morrison, *Science,* 229:1202-1207, 1985; Oi et al., *Bio/Techniques,* 4:214, 1986; U.S. Pat. No. 5,225,539; Jones et al., *Nature,* 321:552-525, 1986; Verhoeyan et al., *Science,* 239:1534, 1988; and Beidler et al., *J. Immunol.,* 141:4053-4060, 1988.

Completely human antibodies are particularly desirable for therapeutic treatment of human patients. Such antibodies can be produced using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, and IgE antibodies. For an overview of this technology for producing human antibodies, see Lonberg and Huszar (*Int. Rev. Immunol.,* 13:65-93, 1995). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Freemont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a murine antibody, is used to guide the selection of a completely human antibody recognizing the same epitope. (Jespers et al., *Biotechnology,* 12:899-903, 1994).

An antibody directed against a glucose transport-related polypeptide (e.g., monoclonal antibody) can be used to isolate the polypeptide by standard techniques, such as affinity chromatography or immunoprecipitation. Moreover, such an antibody can be used to detect the protein (e.g., in a cellular lysate or cell supernatant) in order to evaluate the abundance and pattern of expression of the polypeptide. The antibodies can also be used diagnostically to monitor protein levels in tissue as part of a clinical testing procedure, e.g., for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidinibiotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Methods of Treatment and Pharmaceutical Compositions

Methods of treating disorders related to glucose metabolism are provided herein. "Treating" includes methods that cure, alleviate, relieve, alter, ameliorate, palliate, improve or affect the disorder, the symptoms of the disorder or the predisposition toward the disorder. The methods can be used in vivo or on cells in culture, e.g., in vitro or ex vivo. For in vivo embodiments, the method is effected in a subject and includes administering the agent to the subject under conditions effective to permit the agent to modulate the expression or activity of the polypeptide in a cell.

Agents that modulate expression or activity of a glucose transport-related polypeptide in vitro are further tested in vivo in animal models. For example, a test compound identified as a modulator of a glucose transport-related polypeptide is tested in an animal such as an animal model for obesity or diabetes (e.g., type II diabetes, e.g., ob/ob mice obtained from Jackson Laboratories (Strain Name: B6.V-Lep$^{ob}$/J), db/db mice; see, e.g., Sima A A F, Shafrir E. *Animal Models in Diabetes: A Primer*. Taylor and Francis, Publ Amsterdam, Netherlands, 2000). At various time points after administration of the test agent, levels of expression or activity of the glucose transport-related polypeptide and/or levels of glucose, glucose tolerance, and plasma insulin are monitored to determine whether the test compound has a beneficial effect on glucose metabolism, relative to control, i.e., whether the test compound causes a reduction in hyperglycemia or plasma insulin levels.

Data obtained from the cell culture assays and animal studies can be used in formulating an appropriate dosage of any given agent for use in humans. A therapeutically effective amount of an agent will be an amount that delays progression of or improves one or more symptoms of the condition, whether evident by improvement in an objective sign (e.g., blood glucose levels) or subjective symptom of the disease. Certain factors may influence the dosage and timing required to effectively treat a subject (e.g., the severity of the disease or disorder, previous treatments, the general health and/or age of the subject, and other diseases present).

Compositions useful for modulating expression or activity of the glucose transport-related polypeptides (whether previously known or identified by the screening assays described herein), can be incorporated into pharmaceutical compositions and administered to subjects who have, or who are at risk of developing, a disorder or condition related to glucose metabolism (e.g., related to disregulated glucose metabolism such as type I diabetes, type II diabetes, or obesity). Such compositions will include one or more agents that modulate the expression or activity of the glucose transport-related polypeptide and a pharmaceutically acceptable carrier (e.g., a solvent, dispersion medium, coating, buffer, absorption delaying agent, and the like, that are substantially non-toxic). Supplementary active compounds can also be incorporated into the compositions.

Pharmaceutical compositions are formulated to be compatible with their intended route of administration, whether oral or parenteral (e.g., intravenous, intradermal, subcutaneous, transmucosal (e.g., nasal sprays are formulated for inhalation), or transdermal (e.g., topical ointments, salves, gels, patches or creams as generally known in the art). The compositions can include a sterile diluent (e.g., sterile water or saline), a fixed oil, polyethylene glycol, glycerine, propylene glycol or other synthetic solvents; antibacterial or antifungal agents such as benzyl alcohol or methyl parabens, chlorobutanol, phenol, ascorbic acid, thimerosal, and the like; antioxidants such as ascorbic acid or sodium bisulfite; chelating agents such as ethylenediaminetetraacetic acid; buffers such as acetates, citrates or phosphates; and isotonic agents such as sugars (e.g., dextrose), polyalcohols (e.g., manitol or sorbitol), or salts (e.g., sodium chloride). Liposomal suspensions (including liposomes targeted to affected cells with monoclonal antibodies specific for neuronal antigens) can also be used as pharmaceutically acceptable carriers (see, e.g., U.S. Pat. No. 4,522,811). Preparations of the compositions can be formulated and enclosed in ampules, disposable syringes or multiple dose vials. Where required (as in, for example, injectable formulations), proper fluidity can be maintained by, for example, the use of a coating such as lecithin, or a surfactant. Absorption of the active ingredient can be prolonged by including an agent that delays absorption (e.g., aluminum monostearate and gelatin). Alternatively, controlled release can be achieved by implants and microencapsulated delivery systems, which can include biodegradable, biocompatible polymers (e.g., ethylene vinyl acetate, polyanhydrides, polyglycolic acid, collagen, polyorthoesters, and polylactic acid; Alza Corporation and Nova Pharmaceutical, Inc.).

Where oral administration is intended, the agent can be included in pills, capsules, troches and the like and can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Compositions containing the agents that modulate glucose transport-related polypeptides can be formulated for oral or parenteral administration in dosage unit form (i.e., physically discrete units containing a predetermined quantity of active compound for ease of administration and uniformity of dosage). Toxicity and therapeutic efficacy of compounds can be determined by standard pharmaceutical procedures in cell cultures or experimental animals. One can, for example, determine the $LD_{50}$ (the dose lethal to 50% of the population) and the $ED_{50}$ (the dose therapeutically effective in 50% of the population), the therapeutic index being the ratio of $LD_{50}$: $ED_{50}$. Agents that exhibit high therapeutic indices are preferred. Where an agent exhibits an undesirable side effect, care should be taken to target that agent to the site of the affected tissue (the aim being to minimize potential damage to unaffected cells and, thereby, reduce side effects). Toxicity and therapeutic efficacy can be determined by other standard pharmaceutical procedures.

Data obtained from the cell culture assays and animal studies can be used in formulating an appropriate dosage of any given agent for use in humans. A therapeutically effective amount of an agent will be an amount that delays progression of or improves one or more symptoms of the condition, whether evident by improvement in an objective sign (e.g., blood glucose levels) or subjective symptom of the disease. Certain factors may influence the dosage and timing required to effectively treat a subject (e.g., the severity of the disease or disorder, previous treatments, the general health and/or age of the subject, and other diseases present).

As noted above, agents identified and administered according to the methods described here can be small molecules (e.g., peptides, peptidomimetics (e.g., peptoids), amino acid residues (or analogs thereof), polynucleotides (or analogs thereof), nucleotides (or analogs thereof), or organic or inorganic compounds (e.g., heteroorganic or organometallic compounds). Typically, such molecules will have a molecular weight less than about 10,000 grams per mole (e.g., less than about 7,500, 5,000, 2,500, 1,000, or 500 grams per mole). Salts, esters, and other pharmaceutically acceptable forms of any of these compounds can be assayed and, if a desirable activity is detected, administered according to the therapeutic methods described herein. Exemplary doses include milligram or microgram amounts of the small molecule per kilogram of subject or sample weight (e.g., about 1 µg-500 mg/kg; about 100 µg-500 mg/kg; about 100 µg-50 mg/kg; 10 µg-5 mg/kg; 10 µg-0.5 mg/kg; or 1 µg-50 µg/kg). While these doses cover a broad range, one of ordinary skill in the art will understand that therapeutic agents, including small molecules, vary in their potency, and effective amounts can be determined by methods known in the art. Typically, relatively low doses are administered at first, and the attending physician or veterinarian (in the case of therapeutic application) or a researcher (when still working at the clinical development stage) can subsequently and gradually increase the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The pharmaceutical compositions can be included in a container, pack, or dispenser together with instructions for administration.

The invention will be further described in the following examples which do not limit the scope of the invention described in the claims.

EXAMPLES

Example 1

Identification of Genes and Gene Products that Enhance Insulin Action on Glucose Transport Using RNAi-Screening Cell Culture and Electroporation of 3T3-L1 Adipocytes with siRNA Oligonucleotides.

3T3-L1 fibroblasts were grown in DMEM supplemented with 10% FBS, 50 µg/ml streptomycin, and 50 units/ml penicillin and differentiated into adipocytes as described (Jiang et al., *Proc. Natl. Acad. Sci. USA*, 100:7569-7574, 2003; Guilherme et al., *J. Biol. Chem.*, 279:10593-10605, 2004). The 3T3-L1 adipocytes were transfected with siRNA duplexes by electroporation. Briefly, 4 or 5 days after differentiation was initiated, adipocytes were detached from culture dishes with 0.25% trypsin and 0.5 mg of collagenase/ml in PBS and washed twice with PBS. Cells were washed, counted and resuspended at a density of $9\times10^6$ cells/ml in PBS. Typically, one 150 mm dish was transfected with 6 different siRNA-duplexes. Resuspended cells (0.15 ml) were placed in 0.2 cm gap cuvette (Bio-Rad®) and mixed with 4 nmoles of each SMARTpool® siRNA-duplexes, purchased from Dharmacon. siRNA oligonucleotides were delivered to the cells by a pulse of electroporation with a Bio-Rad® gene pulser II system at the setting of 0.09 kV and 950 µF capacitance. After electroporation, cells were immediately mixed with 1 ml of fresh complete DMEM media. Cells were then transferred from the cuvette to 3 ml of DMEM media in a 15 ml Falcon™ tube and mixed. Aliquots (125 µl) of this cell suspension were seeded into wells of a 96 well plate. Cells from each electroporation were spread into 12 such wells, placed in an incubator and 2-deoxyglucose uptake was measured 72 hours later. The remainder of the cell suspension was distributed equally into 2 wells of a 12 well plate for performing western blot and/or evaluating MAPK and Akt phosphorylation.

For each 2-deoxyglucose assay, cells were also electroporated with scrambled (6 nmoles), Akt1 and Akt2 (4 and 6 nmoles) and PTEN (6 nmoles) siRNAs, as controls. Each 96 well plate contained 12 wells of each of these 3 controls.

2-Deoxyglucose Uptake Assays

Insulin-stimulated glucose transport in 3T3-L1 adipocytes was estimated by measuring 2-deoxyglucose uptake as described (Guilherme et al., *J Biol Chem*, 279:10593-10605, 2004). Briefly, siRNA transfected cells were reseeded on 96-well plates and cultured for 72 hours, washed twice and serum-starved for two hours with Krebs-Ringer's Hepes buffer (130 mM NaCl, 5 mM KCl, 1.3 mM $CaCl_2$, 1.3 mM $MgSO_4$, 25 mM Hepes, pH 7.4) supplemented with 0.5% BSA and 2 mm sodium pyruvate. Cells were then stimulated with insulin for 30 minutes at 37° C. Glucose uptake was initiated by addition of $[1,2-^3H]$ 2-deoxy-D-glucose to a final assay concentration of 500 µM. Cells were incubated for 5 minutes at 37° C. Assays were terminated by three washes with ice-cold Krebs-Ringer's Hepes buffer. Briefly, the plates were dipped into a container with 600 ml of ice-cold Krebs-Ringer's Hepes buffer. Liquids in the wells were drained after each dip by patting the plate on a wad of paper towels. The cells were then solubilized by adding 0.05 ml of 1% SDS per well. Uptake of $[^3H]$ was quantitated using a Microplate scintillation counting instrument. Specific uptake was measured by determining non-specific deoxyglucose uptake in samples incubated in the presence of 20 µM cytochalasin B and subtracting the values obtained for this control from each experimental determination.

Small inhibitory RNAs for approximately 500 different genes were obtained and transfected into adipocytes and tested in deoxyglucose uptake assays described above. A number of genes, when knocked down by transfection of siRNA, resulted in increased or decreased glucose uptake as compared to controls. The results of experiments in which 58 different genes were targeted are depicted in FIG. 1.

The 58 candidate protein kinases selected for gene silencing were identified using Affymetrix GeneChip® array analysis of mRNA isolated from 3T3-L1 preadipocytes versus fully differentiated 3T3-L1 adipocytes using the Bioconductor statistical program, specifically rma and mas5, an implementation of the Affymetrix GeneChip® analysis program (Gentleman et al., *Genome Biol.* 5:R80, 2004). Briefly, total RNA was isolated from 3T3-L1 fibroblast cells grown in culture for 7 days to a quiescent state (Adipocyte Day 0 Differentiation) or from 3T3-L1 adipocytes at day 6, post addition of differentiation media. RNA was isolated from three different days for each replicate. cRNA was fragmented and hybridized to Affymetrix GeneChip® Mouse Expression Set 430 A and 430 B arrays. Raw expression data were analyzed with the Bioconductor statistical environment (Gentleman et al., *Genome Biol.* 5:R80, 2004) using rma (Bolstad et al., *Bioinformatics*, 19:185, 2003) and mas5, a Bioconductor implementation of the MAS 5.0 algorithm (Affymetrix, available on the internet at affymetrix.com). The mas5 program was applied to calculate a present or absent call for each probeset on a GeneChip. The calculation of these calls are based on a Wilcoxon rank test between the PM and MM probes of a probeset. Only the kinases which showed a present call in each of the replicate hybridizations were filtered and used in subsequent analyses.

All kinases were considered expressed in adipocytes if they had mas5 presence calls in each of triplicate hybridizations. Pools of 4 siRNA sequences directed against protein kinases were electroporated into 3T3-L1 cells, and deoxyglucose transport assays on the transfected adipocytes were performed 72 hours later in 96 well plates. In these experiments, scrambled siRNA was used as a control, and siRNA directed against Akt2 protein kinase and the PtdIns(3,4,5)P3 phosphatase PTEN, which function as positive and negative regulators of insulin signaling, respectively, were included.

RNAs targeting the following kinases listed in FIG. 1 caused increased glucose uptake: IKKα, IKKβ, Map4k4, PCTK1, and PFTK1 (marked in FIG. 1 with arrows). Depletion of one kinase, ILK, resulted in decreased uptake (marked with an asterisk in FIG. 1).

Figure 2:
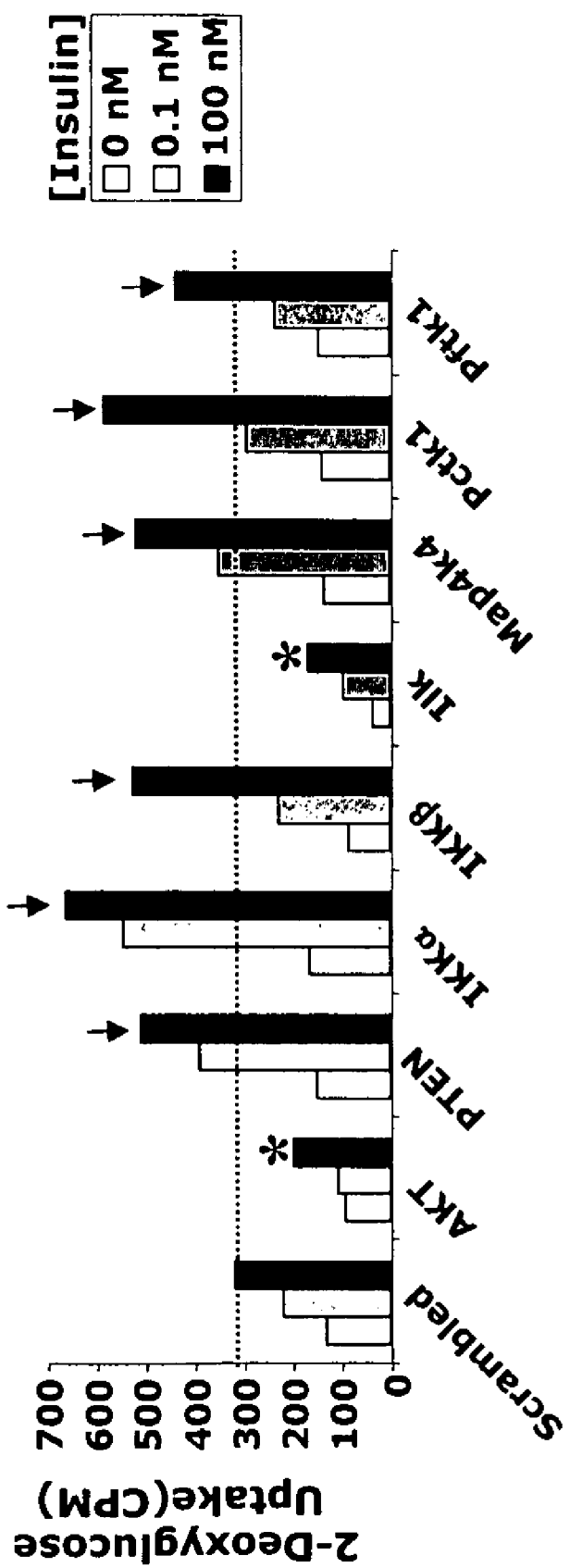
FIG. 2 is a graph depicting the levels and dose dependence of insulin-stimulated deoxyglucose uptake in cells transfected with siRNAs identified in the experiments shown in FIG. 1. Cells were electroporated with controls siRNA or each SMARTpool® (6 nmol) siRNA indicated and assayed as described for FIG. 1. Both positive and negative regulators of glucose transport were examined. The data represents the average of 3 independent screening experiments.

To confirm that siRNA-based gene silencing enhanced insulin-stimulated 2-deoxyglucose uptake in adipocytes, further experiments were performed in which the targets identified by screening were independently retested. The results for experiments with IKKβ, IKKα, ILK, Map4k4, PCTK1, and PFTK1 are depicted in FIG. 2, with scrambled siRNA, AKT2, and PTEN siRNAs used as controls. ILK siRNA inhibited glucose uptake and the other siRNAs increased glucose uptake at both submaximal and maximal doses of insulin in 3T3-L1 adipocytes, confirming the results obtained in previous assays.

In order to further confirm and validate functionality of these protein kinases in cultured adipocytes, a secondary siRNA-based screen was conducted to confirm silencing efficiency and biological effects. PCTAIRE-1, IKKβ and IKKα proteins were substantially decreased by respective siRNA treatments, as determined by Western blot analysis. Similarly, levels of mRNA encoding MAP4K4/NIK and PFTAIRE-1 were decreased by siRNA treatment of cells, as detected by RT-PCR or real time PCR.

Real time PCR was performed as follows. Briefly, total RNA was extracted from the cultured 3T3-L1 adipocytes using Trizol® (Invitrogen). The SuperScript® one-step RT-PCR kit (Invitrogen) was used for RT-PCR. The lower number of cycles was selected to avoid the polymerase chain reaction (PCR) entering plateau stages. For quantitative mRNA analysis, 1 µg of total RNA was reverse transcribed using Bio-Rad's iScript cDNA Synthesis kit (Bio-Rad). Ten percent of each RT reaction was subjected to quantitative real-time PCR analysis using Bio-Rad's iQ SYBR green supermix kit and Real-Time PCR detection system following manufacturer's instructions (MyiQ, Bio-Rad). We designed specific primer pair yielding short PCR product using an online database, PrimerBank (available on the internet at pga.mgh.harvard.edu/primerbank) (Wang and Seed, *Nucleic Acids Res.*, 31(24):e154, 2003). Hyperxanthine-Guantine Phosphoribosyltransferase (HPRT) was used as standard housekeeping gene. Relative gene expression was calculated by subtracting the threshold cycle number (Ct) of the target genes from the Ct value of HPRT and raising 2 to the power of this difference.

Genes for which siRNA targeting resulted in strongly increased and decreased glucose uptake are listed in Tables 1 and 2, above.

Example 2

Characterization of Genes and Gene Products that Modulate Glucose Transport

Western Blotting

3T3-L1 adipocytes electroporated with indicated siRNA were starved overnight in serum-free DMEM media. Cells were then incubated without or with the indicated insulin concentrations for 30 minutes and harvested with lysis buffer containing 1% SDS. Protein concentrations were quantitated and equivalent amounts of protein from each lysate sample were resolved by SDS-PAGE and transferred to nitrocellulose membranes. Membranes were incubated with antibodies overnight at 4° C. and then with horseradish peroxidase-linked secondary antibodies for 45 minutes at room temperature. Proteins were then detected with an enhanced chemiluminescence kit. For experiments described herein, the anti-PTEN, anti-Akt2, anti-Akt, anti-pAkt and anti-lamin A/C antibodies were obtained as described (Jiang et al., *Proc. Natl. Acad. Sci. U S. A.*, 100:7569-7574, 2003). Goat anti-GLUT4, rabbit anti-C/EBPα, anti-C/EBPβ, anti-PCTAIRE-1, mouse anti-PPARγ and anti-SREBP-1 antibodies were from Santa Cruz Biotechnology. Rabbit anti-IKKα and anti-IKKβ were from Cell Signaling Technology (Beverly, Mass.). Mouse monoclonal anti TATA biding protein (TBP) was from Abacam Inc.

Akt Phosphorylation

Figure 3:
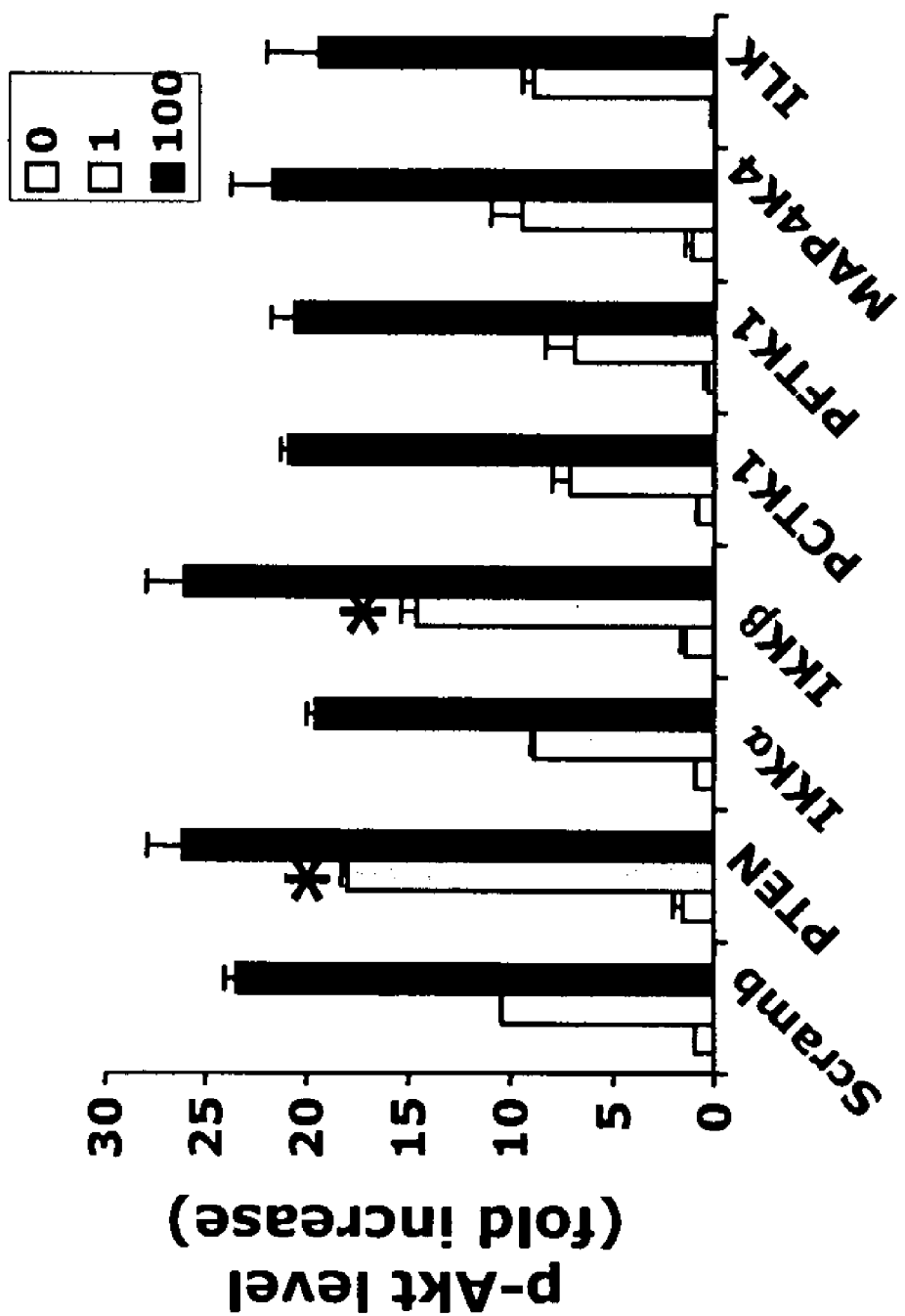
FIG. 3 is graph depicting the effects of RNAi-based silencing of specific genes on insulin-induced Akt phosphorylation. Cultured adipocytes were transfected with scrambled, PTEN, or the indicated SMARTpool® siRNAs by electroporation, reseeded for 72 hours, and serum-starved overnight before treatment with insulin for 30 minutes. Cell lysates were resolved by SDS-PAGE and phospho-(Ser$^{473}$)Akt was detected by Western blotting. Quantitations of phosphorylated Akt are plotted. PTEN and IKKβ enhance insulin-stimulated Akt phosphorylation, as indicated by asterisks. Data are representative of three independent experiments.

The effects of a subset of siRNAs on insulin-induced Akt phosphorylation were examined by Western blotting, as described above. It has been shown that Akt mediates insulin signaling (see Jiang et al., *Proc. Natl. Acad. Sci. USA*, 100: 7569-7574, 2003; and references cited therein). Phosphorylation of Akt at serine 473 is indicative of activation. Adipocytes transfected with scrambled, IKKα, IKKβ, PTEN, PCTK1, ILK, Map4k4, or PFTK1 siRNAs were starved and stimulated with insulin at 0, 1, and 100 nM concentrations. Lysates were resolved by SDS-PAGE and phosphorylation of serine 473 of Akt was analyzed by Western blot. The quantification of the blots is depicted in FIG. 3. IKKβ and PTEN siRNAs enhanced insulin-induced phosphorylation of Akt. Decreased expression of ILK through siRNA action moderately decreased phospho-Akt. In contrast, siRNA-mediated loss of the protein kinases Pctk1, Pftk1, IKKα and MAP4K4/NIK failed to affect the levels of phospho-Akt in the presence or absence of insulin (FIG. 3), indicating they do not modulate insulin signaling to Akt2.

Glucose Transporter Expression

Figure 4:
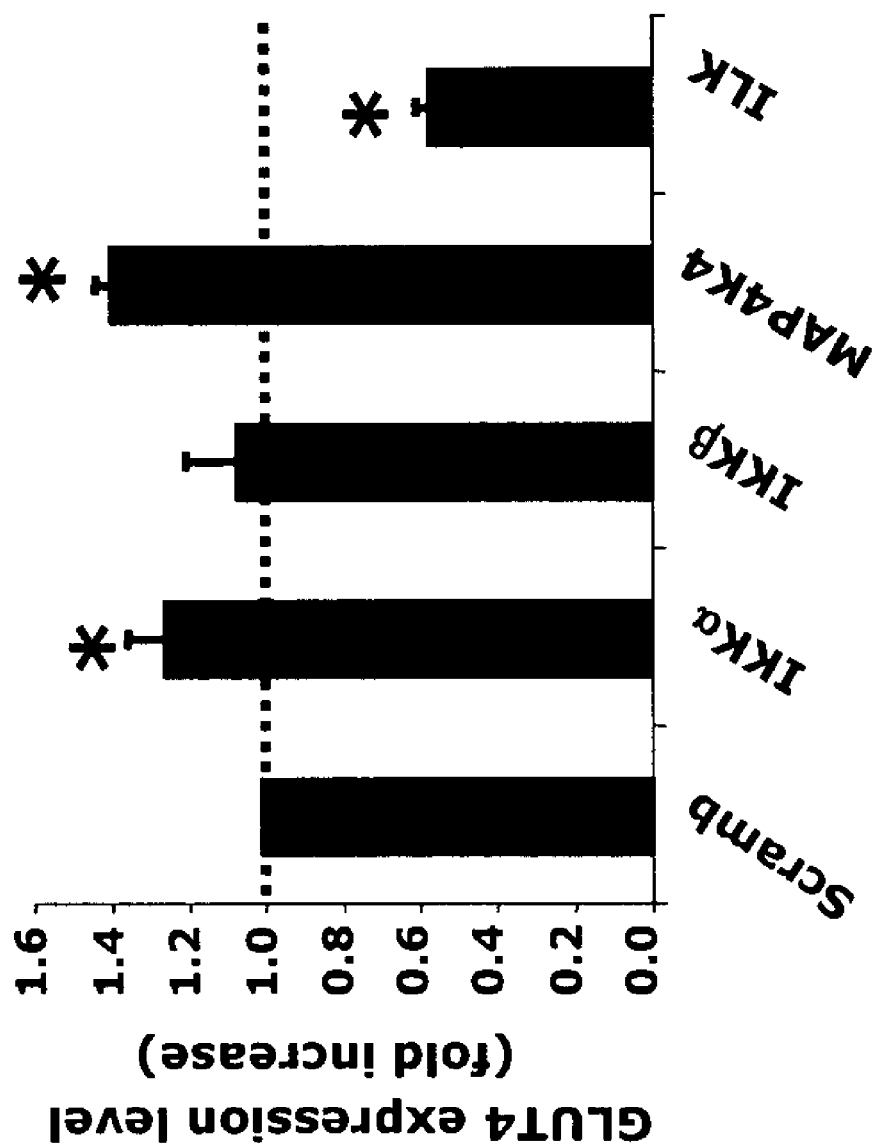
FIG. 4 is graph depicting the effects of siRNA on GLUT4 protein expression. Cultured adipocytes were transfected with scrambled, or the indicated IKKα, IKKβ, Map4K4, or ILK SMARTpool® siRNAs by electroporation, then reseeded and incubated for 72 hours. Cells were lysed and lysates were resolved by SDS-PAGE. Blots were probed with anti-GLUT4 antibody. IKKα and Map4K4, but not IKKβ siRNA enhance GLUT4 protein, as indicated by asterisks. ILK siRNA caused decreased GLUT4 expression (also indicated by an asterisk). Data are representative of three independent experiments.

We next examined whether the depletion of these protein kinases modulate glucose transporter protein levels in 3T3-L1 adipocytes. Depletion of ILK promotes a significant decrease in GLUT4 mRNA and protein, but not GLUT1 protein (FIG. 4).

These data indicate that inhibition of glucose uptake in adipocytes depleted of ILK protein is due to a decrease in GLUT4 protein (FIG. 4) and a small decrease in insulin signaling to Akt (FIG. 3). Depletion of PCTAIRE-1 or PFTAIRE-1 failed to cause detectable changes in GLUT1 or GLUT4-protein levels. In contrast, silencing of IKKα or MAP4K4/NIK expression promoted a significant increase in cellular GLUT4 protein, but not GLUT1 (FIG. 4), potentially accounting for the enhancement of deoxyglucose transport in adipocytes depleted of IKKα or MAP4K4/NIK.

In an attempt to examine whether MAP4K4/NIK also regulates insulin action on GLUT4 recycling, GFP-GLUT4-myc translocation assays (Jiang et al., *Proc. Natl. Acad. Sci. USA*, 100:7569-7574, 2003) were performed in control or MAP4K4/NIK-depleted cells by siRNA. No effect of MAP4K4/NIK depletion was detected in insulin-stimulated GFP-GLUT4-myc translocation (data not shown).

Example 3

Characterization of MAP4K4/NIK Modulation of Glucose Transport

MAP4K4/NIK is Unique Among Expressed MAP Kinases in Attenuating Glucose Uptake in 3T3-L1 Adipocytes.

It has been reported that MAP4K4/NIK may mediate the TNFα stimulation of the SAPK/JNK pathway, through activation of the TAK1→MKK4/MKK7→JNK cascade (Yao et al., *J. Biol. Chem.*, 274:2118-2125, 1999). Large amounts of TNFα are secreted by adipocytes and macrophages within adipose tissue of obese animals (Wellen and Hotamisligil, *J. Clin. Invest.*, 112: 1785-1788, 2003), and this factor is a potent negative regulator of adipogenesis and GLUT4 expression (Zhang et al., *Mol Endocrinol.*, 10:1457-1466, 1996; Stephens et al., *J. Biol. Chem.*, 272:97-976, 1997). TNFα has also been implicated in mediating insulin resistance (Hotamisligil et al., *J. Clin. Invest.*, 95:2409-2415, 1995). Thus, we investigated whether the depletion of other members of the MAPK family, including MAP3K7/TAK1, MAP2K4/MKK4, MAP2K7/MKK7, MAPK8A/JNK1 or MAPK9/JNK2 could also enhance glucose transport in adipocytes.

Figure 5:
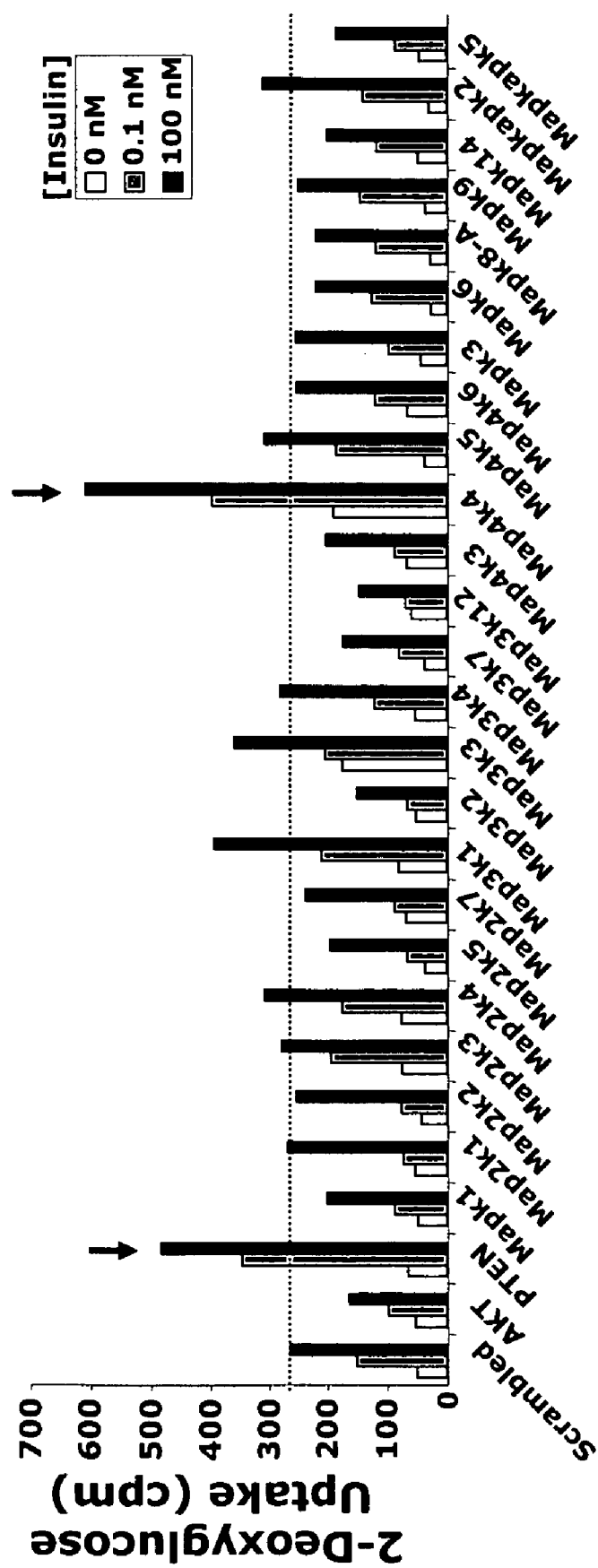
FIG. 5 is a graph depicting the levels and dose dependence of insulin-stimulated deoxyglucose uptake in cells transfected with siRNAs against MAPK family members. Cultured adipocytes were transfected with siRNA pools directed against each of the 22 MAPK family members expressed in adipocytes and deoxyglucose uptake by the cells was determined. Arrows indicate siRNAs that had an effect on deoxyglucose uptake (PTEN and Map4K4).

While attenuation of MAP4K4/NIK expression markedly enhanced insulin-induced glucose uptake, depletion of MAP3K7/TAK1, MAP2K4/MKK4, MAP2K7/MKK7, MAPK8A/JNK1 or MAPK9/JNK2 failed to do so (FIG. 5). Furthermore, FIG. 5 reveals that the effect of MAP4K4/NIK silencing on deoxyglucose uptake is remarkably specific, since electroporation of cultured adipocytes with siRNA pools directed against each of the other 22 MAPK family members expressed in adipocytes did not enhance insulin signaling to deoxyglucose transport. In addition, loss of MAP4K4/NIK in 3T3-L1 adipocytes had no effect on the ability of TNFα to induce phosphorylation of MAPK8A/JNK1 and MAPK9/JNK2 (data not shown). Taken together, these results suggest that the enhancement of insulin-stimulated deoxyglucose transport observed in cells depleted of MAP4K4/NIK is not due to disruption of the TNFα→JNK cascade.

MAP4K4/NIK Attenuates Triglyceride Content, PPARγ and C/EBPα Expression in 3T3-L1 Adipocytes.

Figure 6:
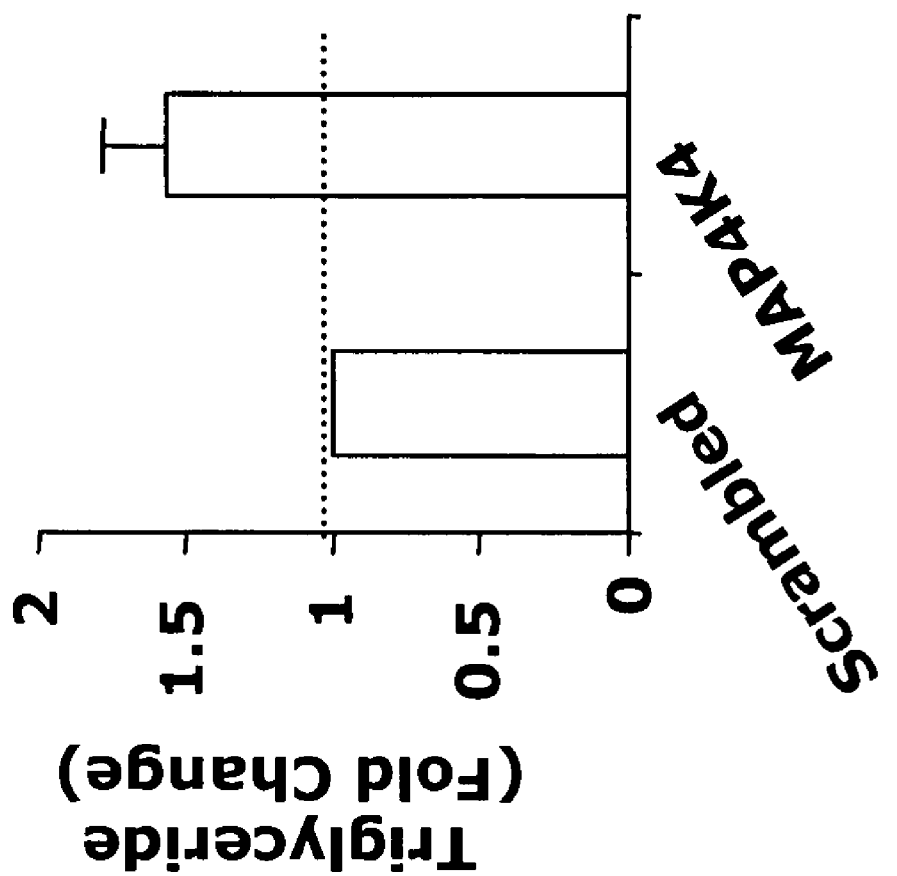
FIG. 6 is a graph depicting the change in triglyceride levels in adipocytes transfected with either scrambled siRNA or Map4K4 siRNA. Data are representative of three independent experiments.

We tested whether MAP4K4/NIK regulates adipocyte differentiation. MAP4K4/NIK depletion in 3T3-L1 cells at 4 days after initiation of differentiation indeed enhanced triglyceride content in the cells measured several days later. Cellular triglyceride content was determined spectrophotometrically using a triglyceride determination kit (Sigma). Cells were rinsed and scraped in PBS. Cell suspensions were sonicated and the triglyceride was measured. MAP4K4/NIK depletion in 3T3-L1 cells at 4 days after initiation of differentiation indeed enhanced triglyceride content in the cells measured several days later (FIG. 6).

Furthermore, Western blots revealed increased expression of the adipogenic transcription factors, C/EBPβ, C/EBPα and PPARγ upon MAP4K4/NIK gene silencing in 3T3-L1 cells. In contrast, no effect on expression of SREBP-1, TBP or the structural nuclear protein Lamin A/C, was observed in these same cells. Taken together, these results suggest that MAP4K4/NIK is unique among the MAP kinases in acting as an endogenous negative regulator of C/EBPβ, C/EBPα and PPARγ expression and adipogenesis in 3T3-L1 cells.

TNFα Treatment and Depletion of PPARγ Enhances MAP4K4/NIK Expression in Cultured Adipocytes.

Figure 7A:
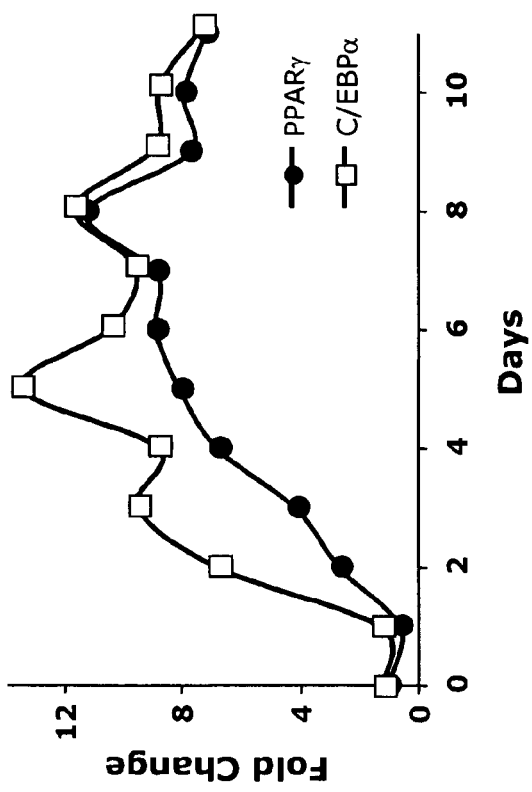
FIGS. 7A and 7B are graphs depicting changes in PPARγ, C/EBPα, and Map4K4 mRNA levels in adipocytes as determined by real time PCR analysis of total RNA isolated during differentiation over 11 days. Data are the averages of two independent experiments and are shown as fold changes over day 0.
Figure 7B:
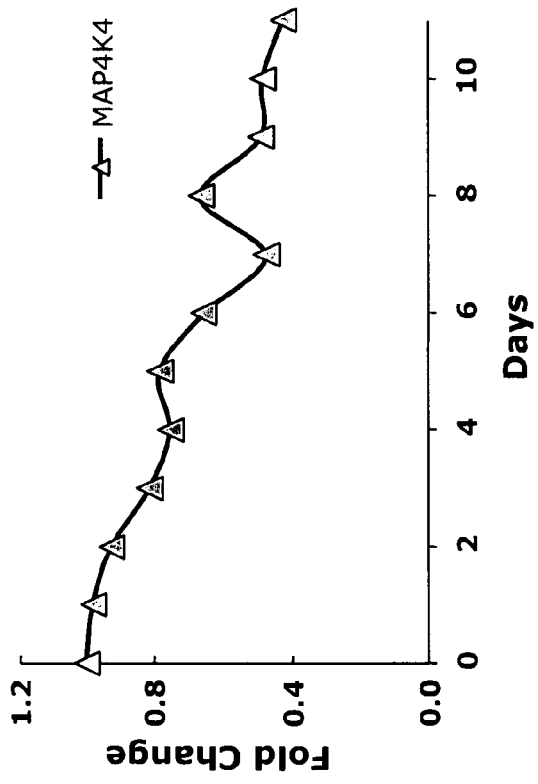
Figure 8:
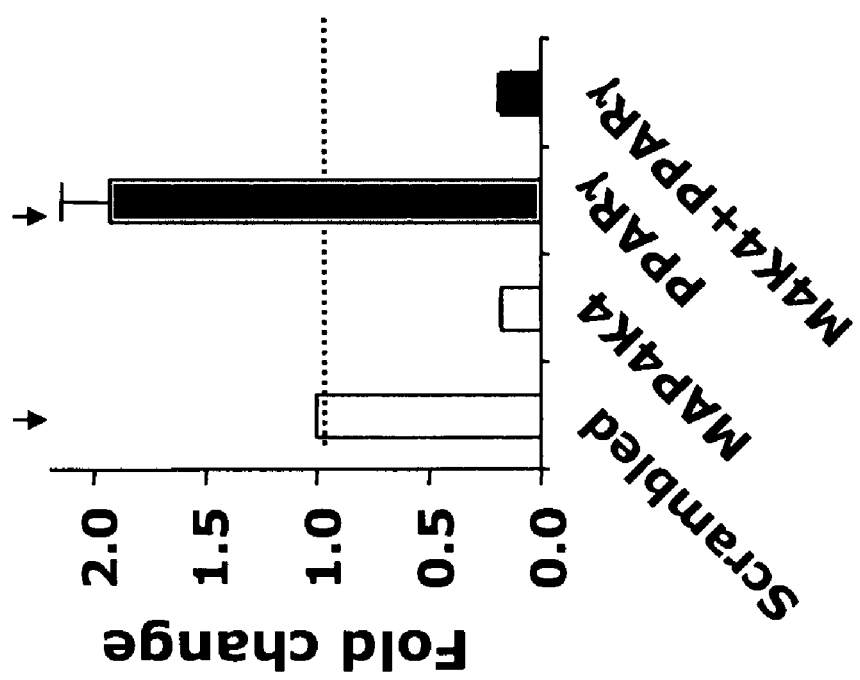
FIG. 8 is a graph depicting changes in Map4K4 levels in adipocytes transfected with scrambled, Map4K4, PPARγ, or Map4K4+PPARγ siRNAs. Adipocytes were transfected with siRNA and replated for 72 hours. RNA was extracted and relative abundance of mRNAs were evaluated by real time PCR analysis. Data represent the average of four independent experiments.

Further analysis of mRNA levels of MAP4K41NIK, PPARγ and C/EBPα during the course of 3T3-L1 cell differentiation revealed an inverse relationship between decreasing expression of MAP4K4/NIK and increasing expression of PPARγ and C/EBPα (FIGS. 7A and 7B). We then tested whether the increased PPARγ expression that occurs during adipogenesis may mediate this decrease in MAP4K4/NIK expression. The expression level of MAP4K4/NIK was examined in fully differentiated 3T3-L1 adipocytes depleted of PPARγ. As depicted in FIG. 8, a highly significant, 2-fold increase in MAP4K4/NIK mRNA level was observed in cultured adipocytes upon attenuation of PPARγ expression with RNAi. Thus, PPARγ acts to inhibit the expression of an inhibitor of adipogenesis, MAP4K4/NIK, while MAP4K4/NIK acts to inhibit the expression of a major promoter of adipogenesis, PPARγ.

In addition to a major role in driving adipogenesis, PPARγ appears to function in mature 3T3-L1 adipocytes by maintaining the expression of genes that confer the characteristics of fully differentiated adipocytes (Morrison and Farmer, *J. Nutr.* 130:3116S-3121 S, 2000; Tamori et al., *Diabetes* 51:2045-2055, 2002). Consistent with these previous observations, attenuation of PPARγ expression by siRNA reduced the abundance of mRNA encoding C/EBPα, GLUT4, PEPCK, aP2, ACS and FAS in mature 3T3-L1 adipocytes (data not shown). Surprisingly, this effect of PPARγ depletion to decrease the abundance of these genes was markedly attenuated when MAP4K4/NIK was also depleted in mature 3T3-L1 adipocytes (data not shown). Together, these data imply that in response to the loss of PPARγ in fully differentiated adipocytes, increased MAP4K4/NIK protein kinase promotes the decay in expression of genes that confer the characteristics of mature adipocytes. These results also indicate that the maintenance of PPARγ-responsive genes in mature adipocytes is achieved in part through the suppression of MAP4K4/NIK expression by PPARγ.

Figures 9A, 9B:
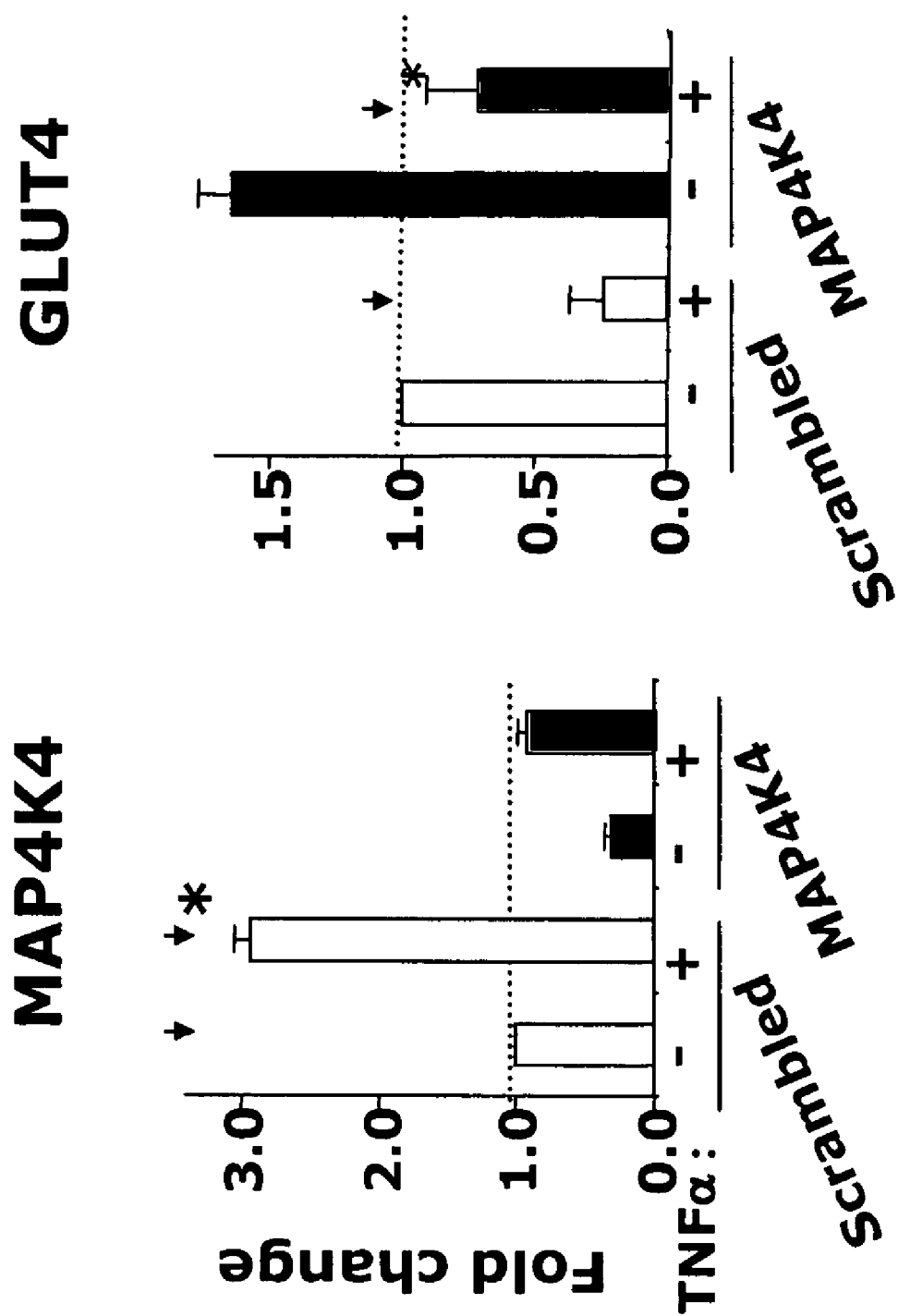
FIGS. 9A and 9B are graphs depicting changes in Map4K4 and GLUT4 levels in adipocytes incubated in the presence or absence of 10 ng/ml TNFα for 24 hours. Adipocytes were electroporated with scrambled or Map4K4 siRNA prior to TNFα treatment. Map4K4 and GLUT4 expression were measured by real time PCR analysis. Data are presented as fold changes over the scrambled siRNA condition and represent the average of three independent experiments.

Finally, we tested whether TNFα, a known negative regulator of adipogenesis and GLUT4 expression, modulates MAP4K4/NIK. Under the conditions of the present experiments, TNFα treatment of 3T3-L1 adipocytes for 24 hours markedly decreased expression of PPARγ and GLUT4, as expected (FIG. 9B). Remarkably, treatment of 3T3-L1 adipocytes with TNFα for 24 hours caused a 3-fold increase in MAP4K4/NIK mRNA levels (FIG. 9A). Depletion of MAP4K4/NIK prior to incubation of cells with TNFα raises the levels of GLUT4 and PPARγ mRNA, and prevents full inhibition of gene expression by TNFα. Thus, these data are consistent with the hypothesis that the increased levels of MAP4K4/NIK that appear in response to TNFα treatment of adipocytes contribute to the attenuation of both adipogenesis and expression of GLUT4 mediated by TNFα. These data indicate that TNFα acts to enhance MAP4K4 expression and to independently suppress PPARγ expression.

Example 4

Evaluating Agents in an Animal Model

Agents that modulate expression or activity of a glucose transport-related polypeptide or nucleic acid encoding the polypeptide in vitro are further tested in vivo in animal models. For example, scrambled siRNA or siRNA that target one or more genes listed in Table 1 are administered to ob/ob mice using hydrodynamic injection as previously described (McCaffrey, *Nature,* 418:38-39, 2002; see also U.S. Pat. Pub. 20030153519). Ob/ob mice can be obtained from Jackson Laboratories (Strain Name: B6.V-Lep$^{ob}$/J). At various time points after administration of the siRNA, mRNA levels for the target(s) from Table 1 are measured. Additionally, the siRNA can be labeled and tracked using methods known in the art. Levels of glucose, glucose tolerance, and plasma insulin can also be monitored to determine whether the siRNA has a beneficial effect on glucose metabolism, relative to control, i.e., whether the siRNA causes a reduction in hyperglycemia or plasma insulin levels.

In one embodiment, siRNAs that target Map4K4 are designed and generated. Briefly, fragments of a particular length (e.g., 23 nucleotides) within the Map4K4 gene sequence are identified, e.g., as described in U.S. Pat. Pub. No. 20040198682. Fragments containing 40-60% GC content and weaker internal fold structure (as determined by in silico analysis) are preferred. Fragments containing strong hairpins and runs of three or more Cs or Gs are avoided. Four or five target fragments are selected and synthesized as siRNA duplexes and screened in vitro to identify the most active siRNAs.

Next, the selected Map4K4 siRNA are tested in ob/ob mice in vivo. To perform hydrodynamic injection, each ob/ob mouse is administered 40 micrograms of the selected Map4K4 siRNA in 1.8 mL of PBS. The siRNA/PBS solution is injected through the tail vein in 4-5 seconds. Levels of Map4K4 expression are determined by examining Map4K4 RNA and/or protein levels in tissues 24 hours, 48 hours, 72 hours, or 4 days after injection. Plasma glucose levels in each animal at 1-3 days following treatment are also measured and compared to controls (e.g., glucose levels prior to siRNA treatment and glucose levels in animals treated with PBS and scrambled siRNA). Map4K4 siRNA that reduce hyperglycemia can be useful in treating glucose transport-related disorders such as diabetes and obesity.

OTHER EMBODIMENTS

A number of embodiments of the invention have been described. Nevertheless, it will be understood that various modifications may be made without departing from the spirit and scope of the invention. Accordingly, other embodiments are within the scope of the following claims.

What is claimed is:

1. A method for increasing insulin-stimulated glucose uptake in a cell in vitro, the method comprising:
   administering to the cell an inhibitory RNA that decreases expression or activity of Mitogen-activated protein kinase kinase kinase kinase 4 (Map4k4) in an amount sufficient to increase insulin-stimulated glucose uptake in the cell, thereby increasing insulin-stimulated glucose uptake in the cell.

2. The method of claim 1, wherein the Map4k4 is human Map4k4.

3. The method of claim 1, wherein the cell is an adipocyte.

* * * * *

UNITED STATES PATENT AND TRADEMARK OFFICE
CERTIFICATE OF CORRECTION

PATENT NO. : 7,790,693 B2
APPLICATION NO. : 11/292549
DATED : September 7, 2010
INVENTOR(S) : Michael P. Czech et al.

It is certified that error appears in the above-identified patent and that said Letters Patent is hereby corrected as shown below:

Please delete the second paragraph in column 1, starting at line 12,

"The work described herein was funded, in part, through grants from the National Institutes of Health (Grant Nos. DK30898 and DK60837-03). The United States government may, therefore, have certain rights in the invention".

Please insert a new paragraph in column 1, starting at line 12, insert a blank line and then insert;

-- FEDERALLY SPONSORED RESEARCH

This invention was made with government support under Grant Nos. DK030648 and DK060837 awarded by the National Institutes of Health. The government has certain rights in the invention. --

Signed and Sealed this

Thirtieth Day of November, 2010

David J. Kappos
*Director of the United States Patent and Trademark Office*